(12) United States Patent
Kramer et al.

(10) Patent No.: US 11,864,901 B2
(45) Date of Patent: *Jan. 9, 2024

(54) DEFLECTABLE MAPPING GUIDE SHEATH FOR HIS BUNDLE PACING

(71) Applicant: St. Jude Medical, Cardiology Division, Inc., St. Paul, MN (US)

(72) Inventors: Scott A. Kramer, Minneapolis, MN (US); Erich W. Stoermer, Plymouth, MN (US); Joshua C. Conway, Wayzata, MN (US); Gene A. Bornzin, Simi Valley, CA (US); Zoltan Somogyi, Simi Valley, CA (US); Amy L. Hanenburg, Minneapolis, MN (US); Emily Weiss, Minneapolis, MN (US); Paul A. Belk, Maple Grove, MN (US); Patrick P. Senarith, Maple Grove, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 81 days.

This patent is subject to a terminal disclaimer.

(21) Appl. No.: 16/967,249

(22) PCT Filed: Feb. 15, 2019

(86) PCT No.: PCT/US2019/018329
§ 371 (c)(1),
(2) Date: Aug. 4, 2020

(87) PCT Pub. No.: WO2019/161286
PCT Pub. Date: Aug. 22, 2019

(65) Prior Publication Data
US 2021/0045644 A1 Feb. 18, 2021

Related U.S. Application Data

(60) Provisional application No. 62/743,460, filed on Oct. 9, 2018, provisional application No. 62/710,431, filed on Feb. 16, 2018.

(51) Int. Cl.
*A61B 5/318* (2021.01)
*A61B 5/287* (2021.01)
(Continued)

(52) U.S. Cl.
CPC .............. *A61B 5/318* (2021.01); *A61B 5/287* (2021.01); *A61M 25/0136* (2013.01); *A61M 25/0147* (2013.01); *A61N 1/056* (2013.01)

(58) Field of Classification Search
CPC .... A61B 5/318; A61B 5/287; A61M 25/0136; A61M 25/0147; A61N 1/056
See application file for complete search history.

(56) References Cited

U.S. PATENT DOCUMENTS

| 5,383,852 A | 1/1995 | Stevens-Wright |
| 5,441,483 A * | 8/1995 | Avitall ............... A61B 18/1492 604/95.05 |

(Continued)

FOREIGN PATENT DOCUMENTS

| CN | 104427950 A | 3/2015 |
| WO | 2007139457 A1 | 12/2007 |

(Continued)

OTHER PUBLICATIONS

International Search Report and Written Opinion from PCT/US2019/018329, dated Jun. 5, 2019, pp. 1-15.

*Primary Examiner* — Catherine M Voorhees
*Assistant Examiner* — Roland Dinga
(74) *Attorney, Agent, or Firm* — Lerner David LLP

(57) ABSTRACT

A delivery device for delivering a pacing lead to the His bundle of a patient's heart includes an elongated sheath having a distal end, and a plurality of mapping electrodes positioned at the distal end. The distal end of the sheath may have a distal tip, and the mapping electrodes may include two electrodes that diametrically oppose one another at a (Continued)

position spaced from the distal tip of the sheath. The sheath includes a plurality of flexible sections spaced apart from one another, and a pull wire that causes the sheath to deflect from a straight configuration to a dual hinged curved configuration that positions the electrodes in the vicinity of the bundle of His.

14 Claims, 18 Drawing Sheets

(51) Int. Cl.
*A61M 25/01* (2006.01)
*A61N 1/05* (2006.01)

(56) References Cited

U.S. PATENT DOCUMENTS

| | | | | |
|---|---|---|---|---|
| 5,454,370 | A * | 10/1995 | Avitall | A61B 5/6857 600/374 |
| 5,916,214 | A * | 6/1999 | Cosio | A61M 25/0141 606/41 |
| 6,926,669 | B1 * | 8/2005 | Stewart | A61M 25/0147 601/3 |
| 7,647,124 | B2 * | 1/2010 | Williams | A61M 25/0041 607/122 |
| 11,413,454 | B2 * | 8/2022 | Guo | A61M 25/0668 |
| 2003/0009095 | A1 * | 1/2003 | Skarda | C22C 14/00 606/41 |
| 2004/0220471 | A1 * | 11/2004 | Schwartz | A61B 5/064 600/424 |
| 2007/0203461 | A1 * | 8/2007 | Williams | A61M 25/0041 604/264 |
| 2007/0270679 | A1 * | 11/2007 | Nguyen | A61M 25/0043 600/585 |
| 2012/0232563 | A1 * | 9/2012 | Williams | A61M 25/0108 606/129 |
| 2013/0231657 | A1 | 9/2013 | Datta et al. | |
| 2016/0045133 | A1 * | 2/2016 | Balachandran | A61B 5/349 600/509 |

FOREIGN PATENT DOCUMENTS

| | | |
|---|---|---|
| WO | 2009006325 A1 | 1/2009 |
| WO | 2014036317 A2 | 3/2014 |
| WO | 2017023798 A1 | 2/2017 |

* cited by examiner

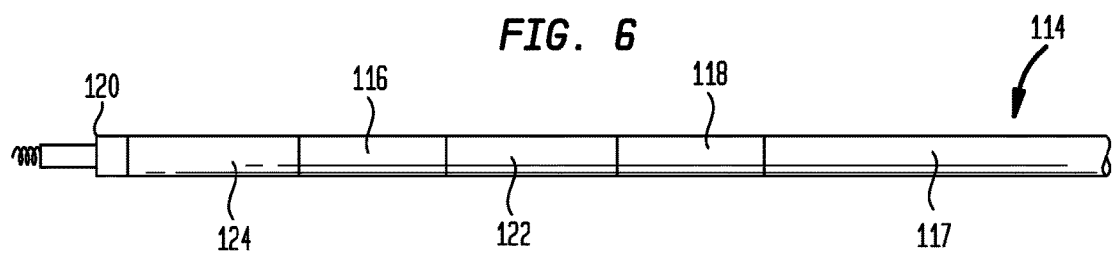
FIG. 6
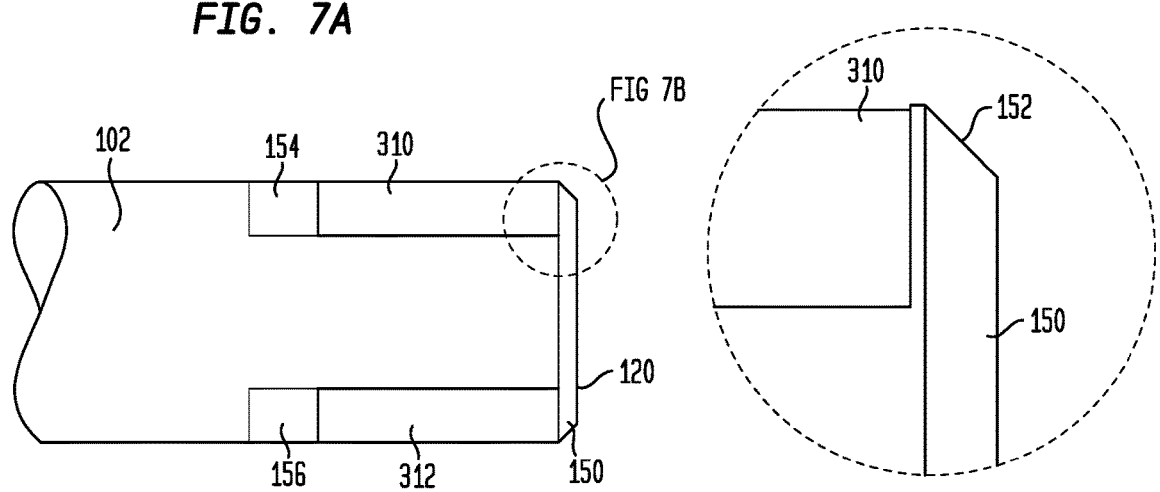
FIG. 7A
FIG. 7B
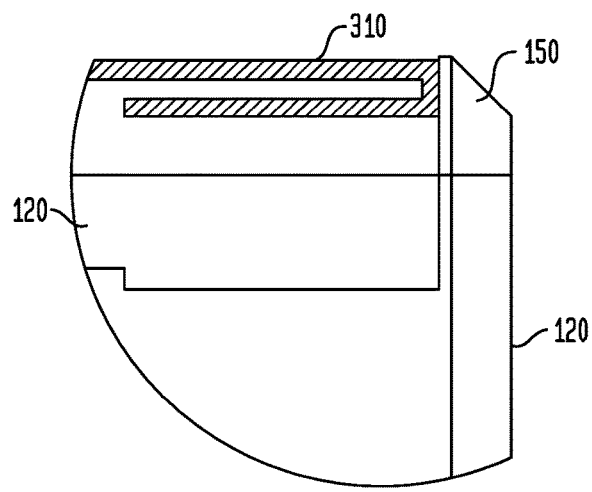
FIG. 7C
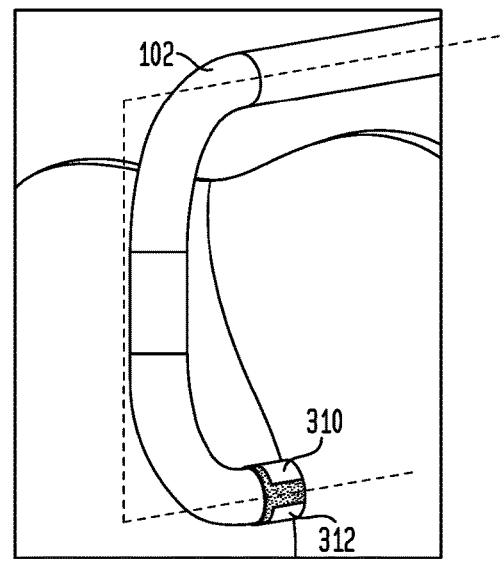
FIG. 7D

DEFLECTABLE MAPPING GUIDE SHEATH FOR HIS BUNDLE PACING

CROSS-REFERENCE TO RELATED APPLICATIONS

The present application is a national phase entry under 35 U.S.C. § 371 of International Application No. PCT/US2019/018329, filed on Feb. 15, 2019, which claims the benefit of the filing dates of U.S. Provisional Patent Application Nos. 62/710,431, filed on Feb. 16, 2018, and 62/743,460, filed on Oct. 9, 2018, the disclosures of which are hereby incorporated by reference herein.

FIELD OF THE INVENTION

The present disclosure relates to cardiac resynchronization therapy (CRT), and more particularly to pacing of the His bundle in the heart of a patient. Still more particularly, the present invention relates to a mapping guide sheath for locating the His bundle and guiding an electrode lead thereto.

BACKGROUND OF THE INVENTION

Cardiac rhythm management systems are useful for electrically stimulating a patient's heart to treat various cardiac arrhythmias. The current standard of care is to pace the right ventricle by myocardial stimulation. In this technique, pacemaker leads are placed at the apex of the right ventricle and at the AV node, the coronary sinus or the left ventricle, and a pacemaker sends electrical pulses to these areas of the heart. While effective, this technique can cause abnormal electrical activation sequences resulting in mechanical ventricular dyssynchrony and an increased risk of heart failure, atrial fibrillation and overall mortality.

An alternative approach has been proposed in which an electrode lead is placed into the bundle of His located either in the septal wall of the right atrium or subvalvular from the right ventricle also in the atrial septum. As part of the electrical conduction system of the heart, the bundle of His transmits electrical impulses from the atrioventricular (AV) node to the ventricles of the heart. As the electrical impulses that regulate the heartbeat are conducted through the bundle of His from the right atrium to the left and right ventricles, a lead placed in or in close proximity to the bundle of His would enable the entire electrical conduction system to be paced in a physiologically natural way. Pacing the ventricles in this manner, which closely mimics normal AV conduction, can greatly reduce or eliminate the risks associated with traditional CRT pacing.

While the improved results obtainable with His pacing have been recognized, in practice His pacing is difficult to achieve because the bundle of His is very small and difficult to locate and access with available devices. The bundle of His has a nominal length of about 5 mm and a nominal width of about 2 mm. It generates an electrical signal that is a small fraction of that generated by the ventricles. As a result of its small size and weak electrical signal, the bundle of His is extremely difficult to find with a conventional pacing lead. Moreover, once the bundle of His has been located, it is difficult to maintain the position of the lead while it is being affixed to the cardiac tissue. The difficulties involved in locating the bundle of His and affixing a pacing lead thereto are reflected in the time it takes to implant the leads of an electrical stimulation device, such as a pacemaker. In a typical case, implanting biventricular leads can be completed in as little as 1 minute. To the contrary, the placement of a single lead for His pacing may take 30 minutes or more, frequently without success. In those cases, the physicians typically revert to conventional lead placement.

There therefore is a need for improvements to the devices used to deliver and implant electrode leads to make it easier to locate the bundle of His and to accurately implant an electrode therein.

BRIEF SUMMARY OF THE INVENTION

One aspect of the present invention provides a delivery device for delivering a pacing lead to the His bundle of a patient's heart. The delivery device includes a handle; an elongated sheath having a proximal end connected to the handle and a distal end remote from the handle, a distal portion of the sheath having a plurality of flexible sections spaced from one another along a length of the sheath; a pull wire having a distal end connected to the sheath distal to the flexible sections and extending to a proximal end; and a plurality of mapping electrodes positioned on the distal end of the sheath.

Another aspect of the present invention provides a method for delivering a pacing lead to the His bundle of a patient's heart. The method includes providing a delivery device having a sheath with an axial lumen and a distal end face; inserting the sheath into the patient's body through the superior vena cava until a distal end portion of the sheath is positioned in the right atrium of the patient; inserting a pacing lead into the axial lumen of the sheath; deflecting the distal end portion of the sheath so that the distal end face of the sheath confronts the wall of the right atrium; and moving the distal end face of the sheath relative to the wall of the right atrium until electrodes on the distal end face of the sheath receive electrical signals from the bundle of His.

BRIEF DESCRIPTION OF THE DRAWINGS

Various embodiments of the present guide sheath and methods for using same are disclosed herein with reference to the drawings, wherein

FIG. 6 is an enlarged view of the distal end of the delivery device sheath;

FIG. 7A is an enlarged side view of the distal tip of the delivery device sheath showing the positions of the mapping electrodes thereon;

FIG. 7B is an enlarged view of a portion of FIG. 7A;

FIG. 7C is a highly schematic enlarged longitudinal cross-section of the illustration shown in FIG. 7B;

FIG. 7D is an enlarged view of the distal end of the delivery device sheath in a deflected condition;

DETAILED DESCRIPTION

As used herein, the terms "proximal" and "distal," when used in reference to a delivery device, are to be taken as relative to a user of the delivery device. "Proximal" is to be understood as relatively close to the user and "distal" is to be understood as relatively far away from the user. As used herein, the terms "substantially," "generally," and "about" are intended to mean that slight deviations from absolute are included within the scope of the term so modified.

Figure 1:
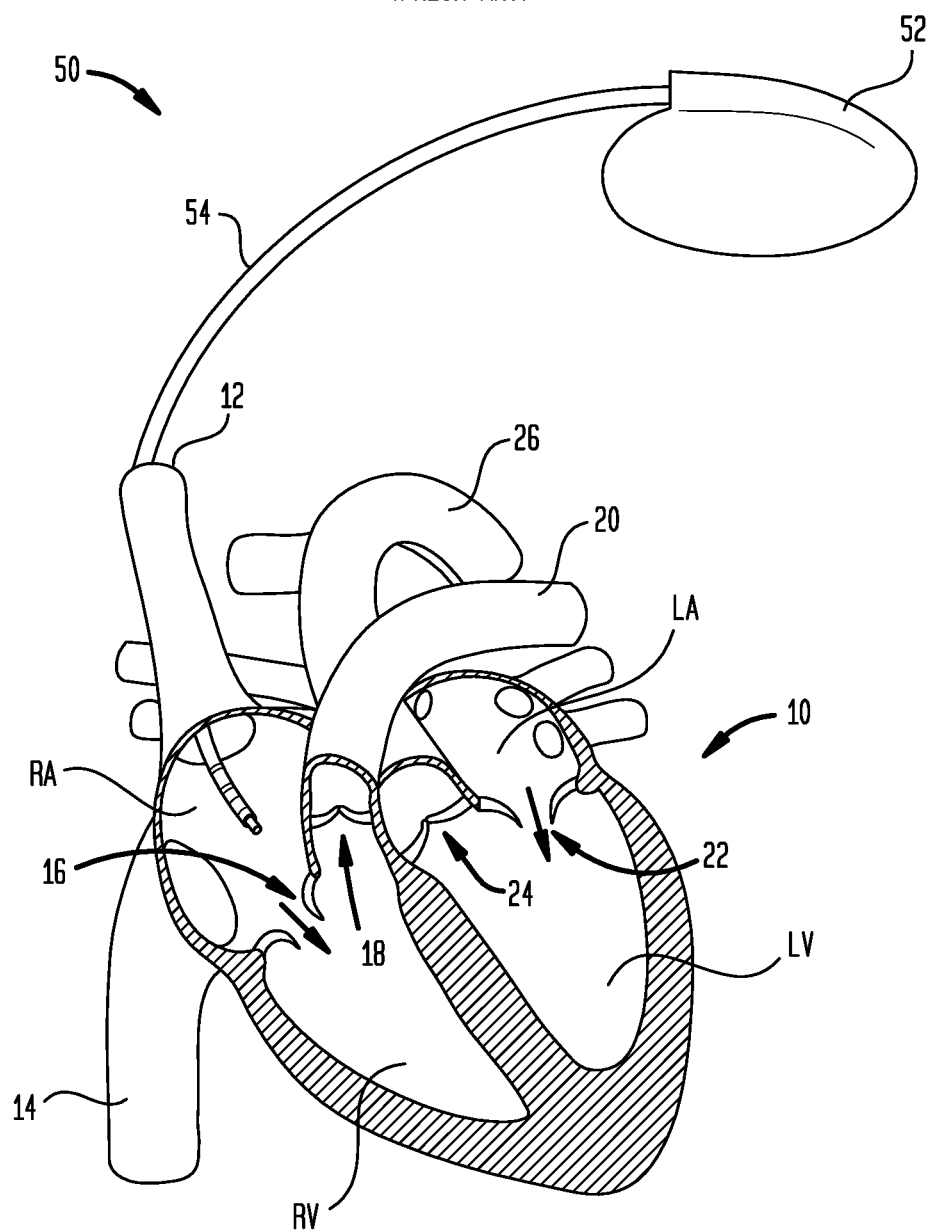
FIG. 1 is a highly schematic cutaway view of the heart illustrating an implantable cardiac pacing system.

FIG. 1 is a highly schematic cutaway view of heart 10 illustrating the right atrium RA, the right ventricle RV, the left atrium LA, and the left ventricle LV. During normal operation of heart 10, deoxygenated blood from the body is returned to the right atrium RA from the superior vena cava 12 and inferior vena cava 14. The right atrium pumps the blood through the atrioventricular or tricuspid valve 16 to the right ventricle RV, which then pumps the blood through the pulmonary valve 18 and the pulmonary artery 20 to the lungs for reoxygenation and removal of carbon dioxide. The newly oxygenated blood from the lungs is transported to the left atrium LA, which pumps the blood through the mitral valve 22 to the left ventricle LV. The left ventricle LV pumps the blood through the aortic valve 24 and the aorta 26 throughout the body.

Figure 2:
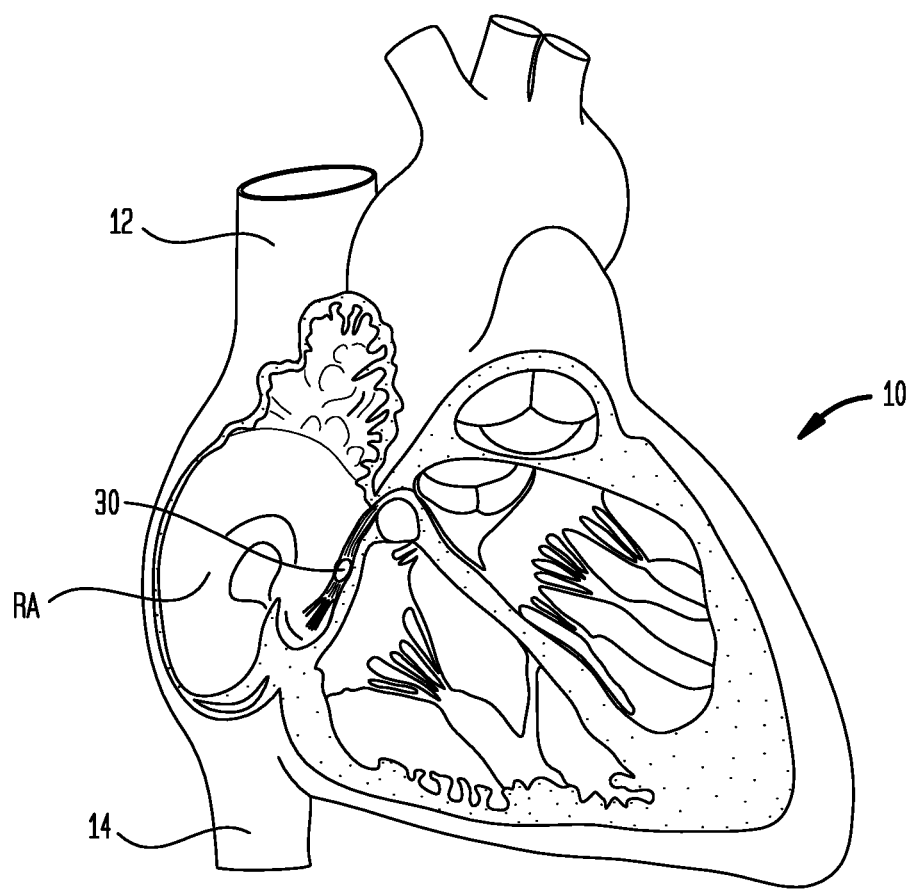
FIG. 2 is a highly schematic cutaway view of the heart showing the position of the His bundle relative to other cardiac structures.

FIG. 2 is another schematic cutaway view showing the location of the bundle of His 30 in the heart. The bundle consists of fast-conducting muscle fibers that begin at the atrioventricular node in the right atrium and pass to the interventricular septum. The bundle divides in the septum into a right branch that travels along the right side of the septum and supplies excitation to the right ventricle, and a pair of left branches that travel along the left side of the septum and supply excitation to the left ventricle. The fibers in the branches terminate in an extensive network of Purkinje fibers which distribute excitation pulses to the layer of cells beneath the endocardium.

Returning to FIG. 1, also shown is a schematic view of a prior art His bundle mapping and pacing system 50. System 50 includes a subcutaneously disposed stimulation device or pacemaker 52 coupled to a pulsing lead 54 designed to penetrate the endocardium in contact with His bundle 30. Lead 54 enters the vascular system through one of several possible vascular access sites and extends through the superior vena cava 12 to the right atrium RA.

Figure 3:
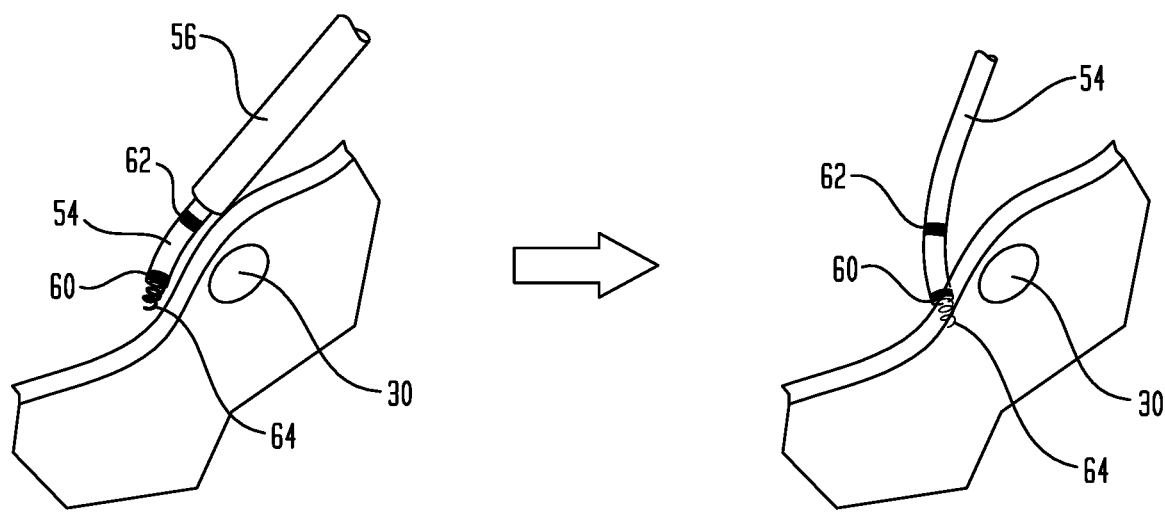
FIG. 3 is a diagrammatic view showing the use of a prior art delivery device to locate and implant a pacing lead near the bundle of His.

FIG. 3 is a diagrammatic view showing the use of lead 54 to locate the bundle of His 30. While it is being maneuvered through the patient's vasculature to the right atrium RA, lead 54 is held within a protective sheath 56. In a conventional system, sheath 56 may have a fixed curve that approximates the position of the bundle of His relative to the superior vena cava 12. Once sheath 56 is in the right atrium, the tip of lead 54 is advanced out from the sheath to expose electrodes 60 and 62 and helical fixation anchor 64. Electrodes 60 and 62 may be spaced apart on lead 54 by up to about 10 mm. Sheath 56 may be manipulated to advance lead 54 parallel to the atrial wall until the faint electrical signals from His bundle 30 are identified. This typically occurs when electrodes 60 and 62 are on opposite sides of the bundle, as depicted in FIG. 3. At this point, sheath 56 may be manipulated to implant fixation anchor 64 in the atrial wall. However, as fixation anchor 64 is distal to electrodes 60 and 62, when the electrodes detect the bundle of His 30, the fixation anchor is at a position spaced several millimeters from the bundle. Hence, if implanted at this location, fixation anchor 64 and lead electrodes 60 and 62 will be offset from the bundle of His, such that any pacing pulses from pacemaker 52 may not stimulate and pace the His bundle.

Figure 4:
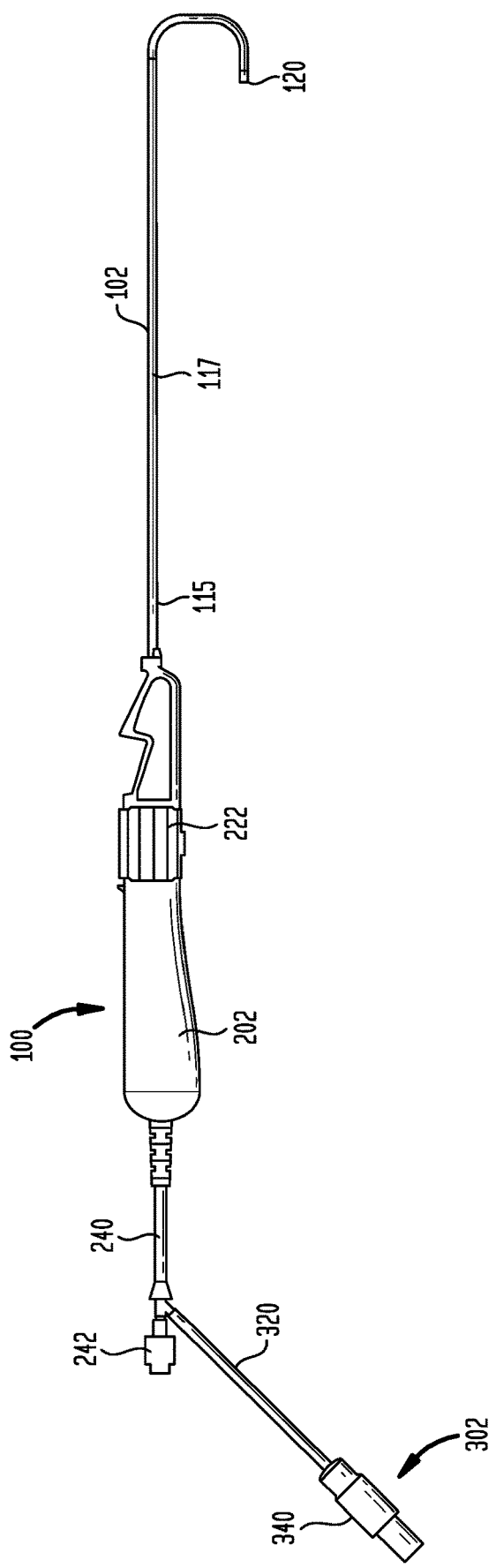
FIG. 4 is a side view of a pacing lead delivery device according to the present disclosure.
Figure 14:
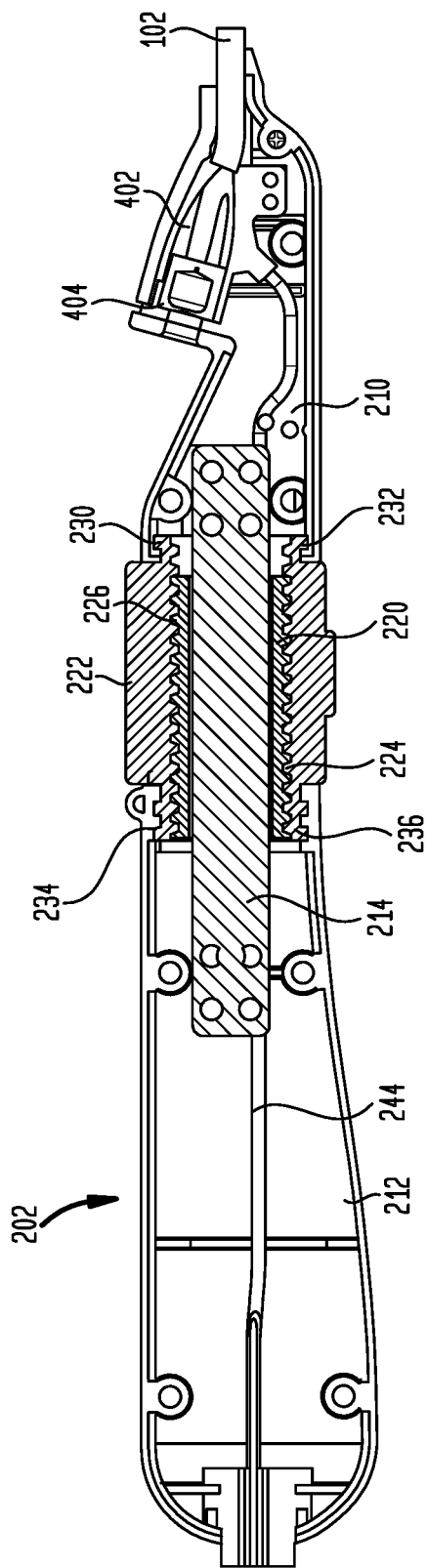
FIG. 14 is a longitudinal cross-section through the handle of the delivery device shown in FIG. 4.

The present disclosure is directed to a delivery device configured to address the foregoing difficulty in locating and implanting lead electrodes in the bundle of His 30. One embodiment of a delivery device 100 according to the present disclosure is shown in FIG. 4. Delivery device 100 includes four major components or assemblies, including a sheath 102, a handle 202, a connector assembly 302, and a hub 402 (FIG. 14). Connector assembly 302 typically includes electrodes mounted on the outer surface of sheath 102 near its distal end and a connector disposed near handle 202. Conductive wires electrically connect the electrodes to the connector. Connector assembly 302 is electrically linked to an external electrogram mapping system. Handle 202 is connected to the proximal end of sheath 102 and includes a mechanism for deflecting the distal end of the sheath. Hub 402 is positioned in handle 202 and has a central opening that accepts the proximal end of sheath 102 and through which a pacing lead is introduced and advanced into the sheath. Each of sheath 102, handle 202, connector assembly 302, and hub 402 is described in more detail below.

Figure 5A:
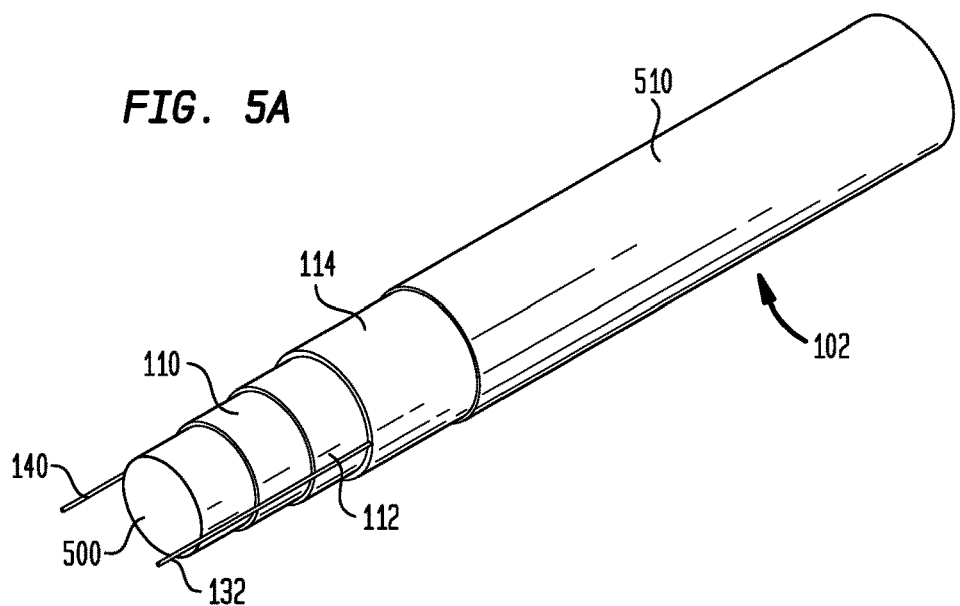
FIG. 5A is a perspective view showing the layers of the delivery device sheath and the components used in assembling the sheath.
Figure 5B:
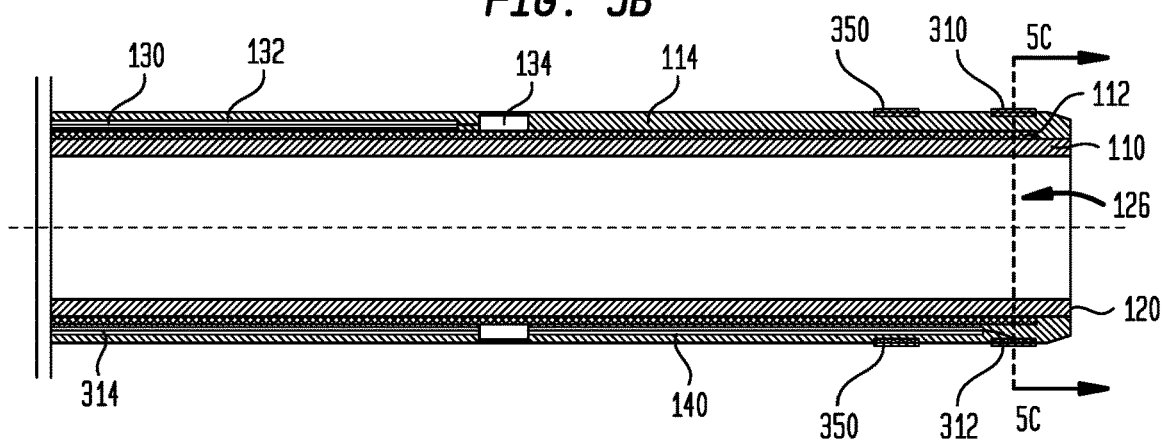
FIG. 5B is a longitudinal cross-section of the delivery device sheath.
Figure 5C:
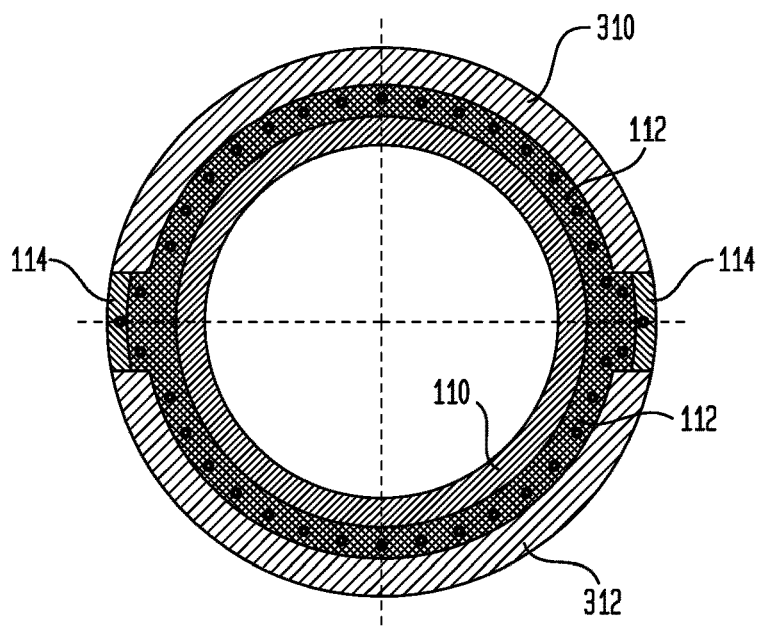
FIG. 5C is a transverse cross-section taken along line 5C-5C of FIG. 5B.

Sheath 102 has a structure and configuration that reliably introduces a pacing lead into a patient's heart, while exhibiting a high degree of maneuverability as well as the ability for its distal end portion to be deflected. It is therefore desirable that sheath 102 have a sufficient degree of columnar strength for advancement through the tortuous vasculature of the patient, and sufficient kink resistance to bend smoothly. Sheath 102 achieves these characteristics from a multi-layer construction as shown in FIGS. 5A-5C. An inner layer 110 of sheath 102 may be formed from a tube of a lubricious material to facilitate the passage of a pacing lead through the sheath, as well as the rotation of the lead within the sheath as it is being fixed to heart tissue. One such lubricious material may be polytetrafluoroethylene (PTFE).

PTFE materials exhibit a high degree of chemical inertness and hydrophobicity, and therefore do not readily adhere to other polymers. In order to integrate inner layer 110 with the other layers of sheath 102, the outer surface of layer 110 may be chemically activated through physical and/or chemical surface treatment methods, including chemical plasma treatment or chemical etching processes known in the art. In one such process, a fluorocarbon etchant containing sodium naphthalene may be utilized to chemically treat the outer surface of layer 110 through a series of process steps, including an etching step, several rinsing steps and a drying step. In the etching step, layer 110 may be immersed in the etchant at a temperature of between about 55° C. and about 65° C. in a tight vessel with nitrogen purging for a duration of between about 30 seconds and a few minutes. Light agitation of the etchant may help promote the etching effect. Following the etching step, the etchant may be drained from the vessel and layer 110 may be subjected to a series of successive rinsing steps, each at a temperature of about 70° C. In the first rinsing step, layer 110 is immersed in an alcohol bath (containing, for example, between about 75 wt % and about 90 wt % isopropanol or methanol) for between about 5 seconds and about 20 seconds. The alcohol chemically deactivates and partially dissolves sodium naphthalene. In the second rinsing step, layer 110 is immersed in chlorine-free carbon-filtered, distilled or deionized water for between about 15 seconds and about 30 seconds. The second rinsing step may be followed by a third rinsing step in which layer 110 is immersed in an acidic water bath (containing between about 2 wt % and about 5 wt % acidic acid) for about 60 seconds. The pH of the acidic water bath should be between about 4 and about 6. The acidity of the bath neutralizes the alkalinity of the etchant and produces a faster and more thorough cleaning effect. Following the rinsing steps, layer 110 may be dried, for example using forced hot air or an oven at between about 70° C. and about 80° C. until fully dried. During the chemical etching of layer 110, the inner lumen thereof should be sealed off or otherwise protected so as to maintain its inherent surface lubricity.

Layer 110 may be followed by a braided layer 112 to provide stability to sheath 102. Braided layer 112 may include a plurality of metallic braids impregnated with one or more thermoplastic polymers. Examples of acceptable thermoplastic polymers include polyamides, such as nylon 11, nylon 12, nylon 612, and the like; polyesters, such as polybutylene terephthalate), poly(ethylene terephthalate), and the like; and thermoplastic elastomers, such as poly (ether-block-amide) copolymer resins, poly(ether-co-ester) block copolymer resins, and various thermoplastic polyurethane block copolymer resins. To form braided layer 112, a first one of the aforementioned thermoplastic polymers may be extruded onto a mandrel whose outer diameter is approximately equal to the lumen diameter of layer 110 to form an inner jacket layer. Multi-thread metallic wires may then be braided over the inner jacket layer. The wires may be round, with diameters of from about 0.02 mm to about 0.2 mm, or flat, with sizes ranging from about 0.01 mm thick by about 0.05 mm wide to about 0.1 mm thick by about 0.20 mm wide. The braid can be woven with a regular, full-load pattern (with one wire passing under two wires and then over two wires), a diamond pattern (with two side-by-side wires alternately passing under two side-by-side wires then over two side-by-side wires), a half-load diamond pattern (with one wire passing under one wire and then over one wire) or other patterns known in the art.

Following the braiding step, another of the aforementioned thermoplastic polymers may be extruded over the braids to form an outer jacket layer. The thermoplastic polymers forming the inner and outer jacket layers can be the same, similar or different. However, they should be chemically compatible or miscible so that the polymer of the outer jacket layer strongly adheres to the polymer of the inner jacket layer as it is extruded thereover. This strong adherence may be achieved by using a polymer with a relatively lower melt temperature for the inner jacket layer and a polymer with a relatively higher melt temperature for the outer jacket layer. As a result, the polymer of the outer jacket layer will thermally fuse and strongly adhere to the polymer of the inner jacket layer, embedding the metallic braids therebetween.

Sheath 102 further includes an outer polymer layer 114 disposed over braided layer 112. Outer layer 114 preferably provides columnar strength in the proximal and middle sections of sheath 112 and deflectability in the distal section of the sheath. Layer 114 may be formed from any polymer capable of being extruded to the desired dimensions and of providing the proper stiffness and stability, including any of the thermoplastic polymers described above for forming braided layer 112. One such material is a polyether block amide sold under the name Pebax® by Arkema France. The proximal section 115 and middle section 117 of outer layer 114 may be formed from a tube of a polymer having a hardness of about 60 to about 100 on the Shore D scale as measured by a durometer, with a Shore D hardness of about 70 to about 75 being preferred. In a distal section of sheath 102, shown more clearly in FIG. 6, layer 114 includes two sections 116 and 118 of a less hard, and therefore more pliable, material. Sections 116 and 118 may also be formed from tubes of Pebax® polyether block amide or another thermoplastic elastomer, but with a Shore D hardness of between about 20 and about 40, preferably about 35. Sections 116 and 118 each may have a length in the axial direction of sheath 102 of between about 1 cm and about 3 cm. In a preferred arrangement, each of sections 116 and 118 may have a length in the axial direction of sheath 102 of between about 1.5 cm and about 2 cm. The distalmost section 116 may be spaced from the distal end 120 of sheath 102 by between about 1 cm and about 3 cm, preferably by between about 1.5 cm and about 2.5 cm. The proximalmost section 118 may be spaced from section 116 by between about 0.5 cm and about 2 cm, preferably by between about 1 cm and about 2 cm. The section 122 of outer layer 114 between sections 116 and 118, and the section 124 of layer 114 between distal end 120 and section 116 are preferably made from the same relatively rigid material as the proximal section 115 and middle section 117 of the outer layer. Sections 116 and 118 may be joined to the other sections of layer 114 by gluing, ultrasonic welding, reflow heating or other known techniques. In a preferred arrangement, the distal tip of sheath 102 may be formed from Pebax® or another polymer that is softer than the material forming section 124 so as to provide an atraumatic tip to the sheath. In some embodiments, the polymers forming layer 114 may include radiopaque fillers, such as barium sulfate, tungsten, bismuth trioxide, bismuth subcarbonate, bismuth oxychloride and the like. Polymers containing a radiopaque filler may be used for outer layer 114 in different sections of sheath 102. A lumen 126 extends continuously through sheath 102 from distal end 120 to handle 202. Lumen 126 has a diameter that is slightly larger than the diameter of the pacing lead to be delivered to the heart by delivery device 100. For example, for a 7 French pacing lead (having a diameter of about 2.33 mm), lumen 126 may have a size of about 7.5 French (a diameter of about 2.5 mm).

A pull wire 130 may extend through a narrow tube 132 extending along the length of sheath 102 between braided layer 112 and outer layer 114. In an alternate arrangement, tube 132 may be positioned between inner layer 110 and braided layer 112. Tube 132 is preferably formed from a material that will resist collapsing or kinking during the manufacture of sheath 102 and the use of delivery device 100. Materials appropriate for forming tube 132 include polyetherimide, polyimide, PTFE or other high temperature polymers. Optionally, tube 132 may include metal braids to further enhance its kink resistance. Pull wire 130 may be affixed at its distal end to a pull wire ring 134 and at its proximal end to an operating mechanism in handle 202, described more fully below. Pull wire ring 134 is located distally of sheath section 116 near the distal end 120 of the sheath, and is fixed in place between braided layer 112 and outer layer 114.

Near its distal end 120, sheath 102 includes a pair of split ring mapping electrodes 310 and 312, as shown in FIGS. 5B and 7A. Electrodes 310 and 312 are part of connector assembly 302, and they may be identical to one another. Any appropriate metal, such as platinum-iridium, may be used to form electrodes 310 and 312, and they may be diametrically opposed to one another on opposite sides of sheath 102. For a sheath having a conventional size, the ends of electrode 310 may be spaced apart in the circumferential direction from the ends of electrode 312 by between about 1 mm and about 3 mm, preferably by about 2.5 mm. An electrical conductor 314 may extend from each of electrodes 310 and 312 through a narrow tube 140 extending along the length of sheath 102 between braided layer 112 and outer layer 114 or between inner layer 110 and braided layer 112. Tube 140 may be formed from the same polymer used to form tube 132, and may optionally include metal braids to enhance its kink resistance. Upon exiting tube 140, conductors 314 may travel through a lumen (not shown) in handle 202 and through a conduit 320 to an electrical connector 340.

To fabricate sheath 102, its individual components may be sequentially assembled over a supporting core rod 500. Thus, after treatment of its outer surface, inner layer 110 may be assembled over core rod 500, followed by braided layer 112. Pull wire ring 134 may then be positioned over braided layer 112 near the distal end of sheath 102, and tubes 132 and 140 may be positioned alongside the braided layer. Alternatively, tubes 132 and 140 may be positioned against inner tube 110 and braided layer 112 may be assembled thereover. Pull wire 130 may be threaded from pull wire ring 134 through tube 132 and out from the proximal end thereof. Similarly, electrical conductors 314 may be threaded through tube 140 and out from the proximal end thereof. As will be appreciated from the discussion below, tube 132 and pull wire 130 preferably are positioned along the side of braided layer 112 toward which sheath 102 is to be deflected. Tube 140 and electrical conductors 314 may be positioned on the side of braided layer 112 diametrically opposed to tube 132 or at another position around the circumference of the braided layer. Sections 115, 117 (which together may comprise a single tube), 116, 118, 120 and 122 of outer layer 114 may then be assembled over the previously assembled components. When all of the individual components of sheath 102 have been assembled together and their relative positions have been properly adjusted, a heat-shrinkable tube 510 may be applied to fully encapsulate the assembly. When heated in a reflow process to an appropriate thermal lamination temperature near or above the critical thermal transition temperatures of the polymers used for braided layer 112 and outer polymer layer 114, those layers will partially or completely melt, thermally bonding the layers to one another and to inner layer 110. Although the inner layer 110 will not melt, the chemical etching of its surface will cause the polymers of braided layer 112 to strongly adhere to it.

Although braided layer 112 was described above as including metal braids embedded in inner and outer polymer jacket layers, that may not be the case. In an alternate embodiment, braided layer 112 can be formed simply by forming the metal braids on a disposable mandrel without the polymer jacket layers. In such arrangement, the individual components of sheath 102 would be assembled as described above, with the metal braided layer 112 assembled over inner layer 110 (and over or under tubes 132 and 140), and, with pull wire 130, pull wire ring 134, and conductors 314 properly positioned, the sections of outer layer 114 may be assembled thereover. During the subsequent reflow process, the polymers of outer layer 114 will melt, permeate the metal braids and fuse to inner layer 110.

As electrodes 310 and 312 are split ring electrodes that do not fully circumscribe sheath 102, the electrodes must be strongly attached to the sheath so as to not become detached therefrom upon advancement of the sheath through the patient's vasculature to deliver a pacing lead to the bundle of His 30 or during removal of the sheath from the patient following such procedure. Thus, while electrodes 310 and 312 may be positioned at the tip of sheath 102 to thereby be exposed on the distal end face of the sheath, the electrodes are preferably spaced from the tip of the sheath so as to be surrounded on all sides by a continuous mass of the sheath polymer.

FIGS. 7A-C illustrate the positions of electrodes 310 and 312 at the distal end 120 of sheath 102. The positions of electrodes 310 and 312 on sheath 102 are based generally on two considerations—obtaining the strongest signal from the bundle of His, and assuring the adherence of the electrodes to the sheath. As noted, it is preferably to space electrodes 310 and 312 from the tip of sheath 102 to more securely adhere the electrodes to the sheath. However, the ability of the electrodes to sense signals from the bundle of His is greatest when the electrodes are exposed on the distal end face of the sheath. As a compromise, it is preferable to position the electrodes as close as possible to the distal end face of sheath 102 while still allowing a region 150 of polymer between the electrodes and the tip of the sheath. In one embodiment, recessing the electrodes about 0.5 mm from the tip of sheath 102 is preferred. In addition to more securely fixing the electrodes to sheath 102, spacing the electrodes proximally of the distal tip of the sheath keeps sharp edges of the electrodes from being exposed, thereby reducing trauma to tissue as delivery device 100 is advanced through the patient's vasculature. As shown in FIG. 7B, the tip of sheath 102 also may be chamfered, as at 152, further reducing trauma during the advancement of delivery device 100. Making the distal end of sheath 102 black or another dark color, as shown in FIG. 7D, will highlight metallic electrodes 310 and 312 and make them more visible.

Another consideration in where to position electrodes 310 and 312 on sheath 102 has to do with the direction in which the distal tip of the sheath deflects. In that regard, it is preferable to position the electrodes on sheath 102 so that, when the sheath is deflected, the electrodes are generally aligned in the direction in which the fibers of the bundle of His are oriented. The maximum signal will be detected from the bundle of His when both electrode 310 and electrode 312 are located directly thereover. Thus, if electrodes 310 and 312 are oriented on sheath 102 on opposite sides of the deflection plane defined by the deflected distal tip of the sheath (i.e., at positions located 90° from the positions shown in FIG. 7D), only one electrode at a time will be able to be located over the His bundle 30. As sheath 102 is moved relative to the atrial septal wall in an area in close proximity to the His bundle, one electrode may move closer to the His bundle while the other electrode may move away from the His bundle, such that the maximum possible signal will not be obtained. On the other hand, by positioning both of electrodes 310 and 312 in the deflection plane, as shown in FIG. 7D, both electrodes can lie over the bundle of His 30 at the same time. In fact, as sheath 102 is moved across the atrial septal wall, there will be a distance equal to about the diameter of the sheath within which the maximum His bundle signal can be detected.

In order to assemble electrodes 310 and 312 to sheath 102, a portion of the polymer is first removed from areas on opposite sides of the distal end of the sheath, creating cavities 154 and 156 sized to receive the electrodes. Cavities 154 and 156 may be formed either before or after assembling the components of sheath 102. In one example, the polymer may be removed by laser ablation, although other removal techniques known in the art may also be employed, including but not limited to cutting, grinding, chemical etching and the like. Preferably, the polymer is removed to a depth that is substantially the same as the radial thickness of electrodes 310 and 312 so that, once assembled to sheath 102, the outer surface of the electrodes will be substantially flush with the outer surface of the sheath. After conductor 314 has been assembled to each of electrodes 310 and 312, the electrodes are inserted into cavities 154 and 156, respectively, and the distal end of the sheath may again be subjected to a reflow heating process to partially or completely melt the outer polymer of braided layer 112 and outer polymer layer 114 to mechanically bond the electrodes to the sheath. FIG. 7C is a cross-sectional view showing electrode 310 embedded within the polymer at the distal end of sheath 102.

FIGS. 8-13 illustrate examples of structures for forming electrodes 310 and 312 to facilitate their secure assembly to sheath 102. Each of the curved structures shown in these figures may be laser cut or otherwise formed from a metal tube having a circumference that is substantially similar to the circumference of sheath 102 so that the curvature of the resultant electrodes matches that of the sheath. Structures not shown with a curved configuration may be formed flat from flat sheet stock and subsequently bent to have a curvature that matches the curvature of sheath 102.

Figure 8:
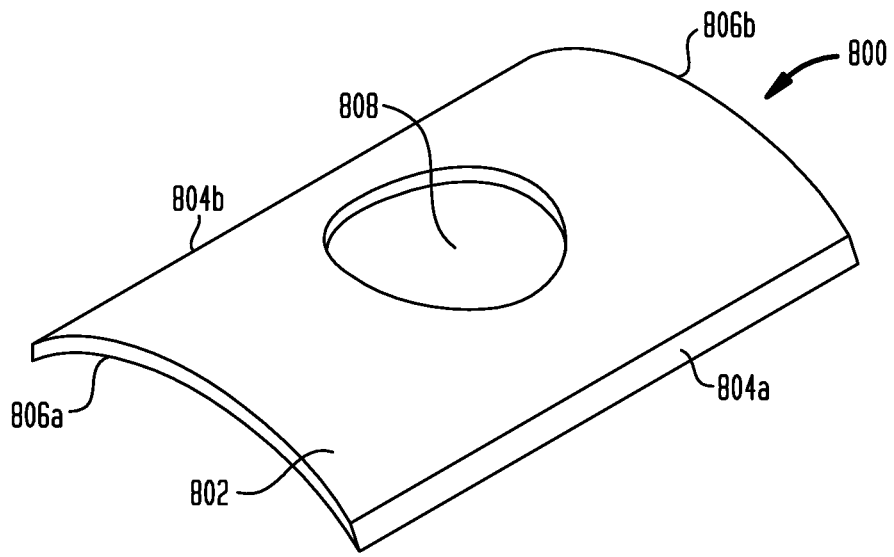
FIG. 8 is a perspective view of one embodiment of a sheath electrode.

The electrode 800 shown in FIG. 8 is generally in the form of a plate 802 having a curvature that is substantially similar to the curvature of the outer surface of sheath 102. The side edges 804a and 804b of plate 802 (i.e., the edges that are substantially parallel to the longitudinal axis of sheath 102) are beveled so that, during the reflow heating process, the softened or molten polymer can flow over the beveled edges to securely hold electrode 800 to the sheath. Rather than the side edges of plate 802 being beveled, electrode 800 may be formed so that the end edges 806a and 806b of plate 802 (i.e., the edges that are substantially orthogonal to the longitudinal axis of sheath 102) may be beveled, or both the side edges and end edges may be beveled. Plate 802 may optionally include an aperture 808 that may fill with polymer during the reflow heating process to further prevent electrode 800 from moving longitudinally relative to the sheath.

Figure 9:
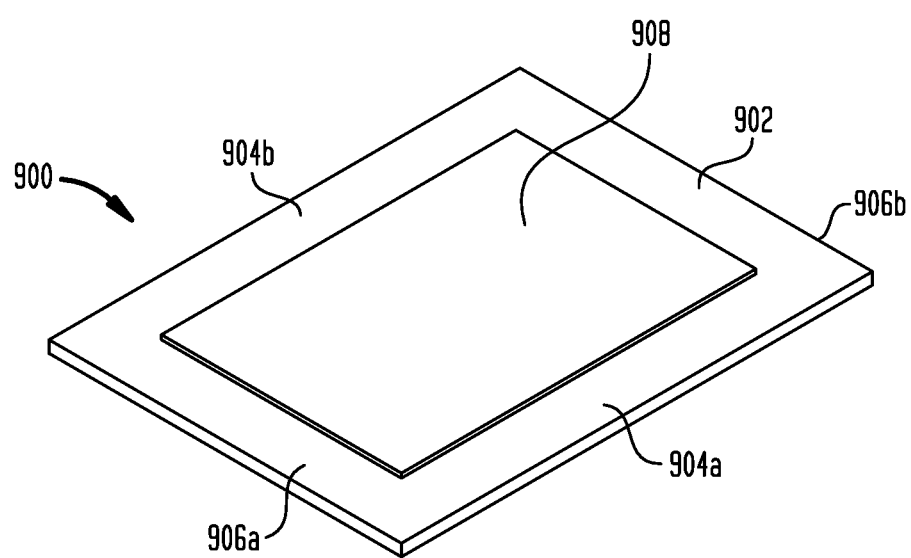
FIG. 9 is a perspective view of another embodiment of a sheath electrode.

In the embodiment shown in FIG. 9, a generally flat metal plate 902 may be formed with a reduced thickness along its side edges 904a and 904b and end edges 906a and 906b. This reduced thickness may be formed by a stamping operation, by grinding, machining or other mechanical technique, by chemical etching or by other known techniques. As a result, the thickness of the side and end edges of plate 902 may be less than the thickness of a center region 908. Once the edges of plate 902 have been thinned, the plate may be deformed into an electrode 900 having a curved shape that substantially matches the curvature of sheath 102. Following the attachment of conductor 314, an electrode 900 may be assembled in each of cavities 154 and 156 and the distal end of sheath 102 may be subjected to a reflow heating process. During such process, the softened or molten polymer will flow to cover the thinned edges of electrodes 900 to firmly hold same in place.

Figure 10:
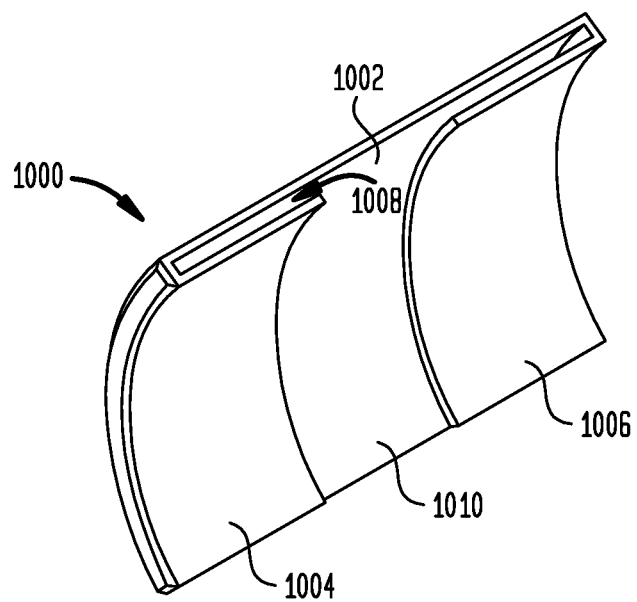
FIG. 10 is a perspective view of yet another embodiment of a sheath electrode.

FIG. 10 shows an electrode 1000 that is generally in the form of a rectangular plate 1002 having a curvature that is substantially similar to the curvature of the outer surface of sheath 102. The end portions 1004 and 1006 of plate 1002 are bent toward one another against the inner surface of plate 1002 as in a conventional staple so that a slight gap 1008 is formed between end portions 1004 and 1006 and the main body 1010 of the plate. Following the attachment of conductors 314, electrodes 1000 may be assembled in appropriate positions near the distal end of sheath 102 and the sheath may be subjected to a reflow heating process. As the polymer of sheath 102 softens, electrodes 1000 may sink into the polymer, and the polymer may flow into the gaps 1008 between end portions 1004 and 1006 and main body 1010, securely affixing the electrode to the sheath. Thus, preforming cavities 154 and 156 in sheath 102 may not be necessary in this embodiment. While FIG. 10 shows end portions 1004 and 1006 bent at right angles to the sides of plate 1002, that need not be the case. End portions 1004 and 1006 may be bent at an angle other than right angles if it is desired to produce a non-rectangular electrode surface.

Figure 11:
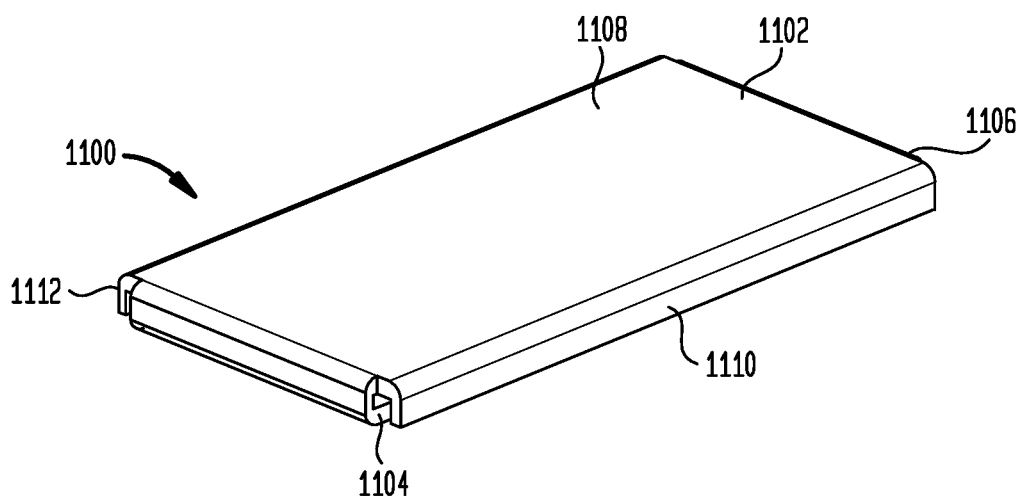
FIG. 11 is a perspective view of still a further embodiment of a sheath electrode.

FIG. 11 shows an electrode 1100 which is a variant of electrode 1000 shown in FIG. 10. The difference between the electrodes is that, in addition to main body 1108 and end portions 1104 and 1106, the plate 1102 of electrode 1100 includes projections 1110 and 1112 that protrude from the lateral sides of the main body. In addition to folding the end portions 1104 and 1106 of plate 1102 against the inner surface of the plate, projections 1110 and 1112 may be folded inwardly until they cover the side edges of the end portions. Relative to electrode 1000, electrode 1100 eliminates exposed sharp edges that could damage tissue, and provides a more secure affixation of the electrode to sheath 102, particularly in the circumferential direction.

Figure 12A:
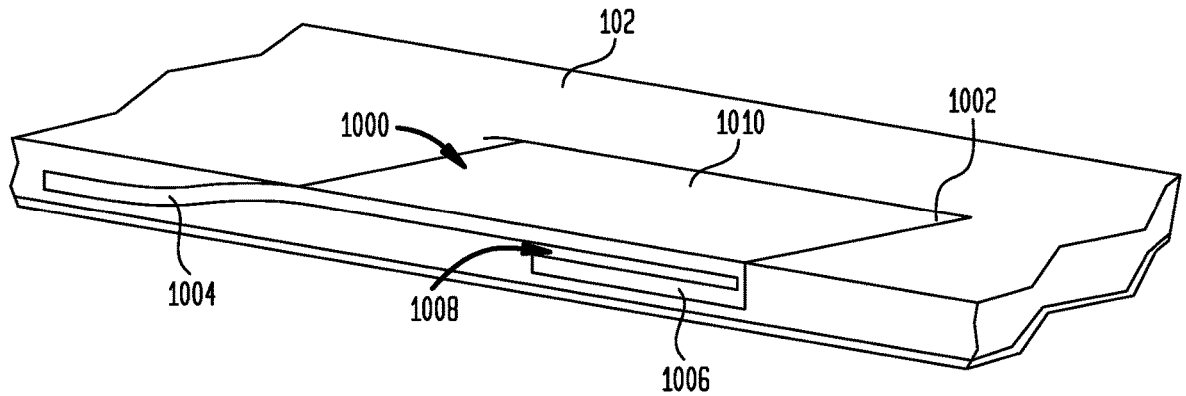
FIGS. 12A-D are highly schematic longitudinal cross-sections of the sheath electrode of FIG. 10 embedded in a sheath.

Different configurations for securing the electrode 1000 of FIG. 10 to sheath 102 are shown in the longitudinal cross-sectional views shown in FIGS. 12A-D. In each configuration, following the attachment of a conductor 314 to each electrode 1000, one electrode is placed into each of cavities 154 and 156 and the distal end of sheath 102 is subjected to a reflow heating process, locking the electrodes in place. Referring to FIG. 12A, rather than bending the end portions 1004 and 1006 of plate 1002 toward one another, end portion 1006 is bent toward the inner surface of plate 1002, while end portion 1004 is bent away from end portion 1006 and main body 1010 so that end portions 1004 and 1006 lie in substantially the same plane.

Figure 12B:
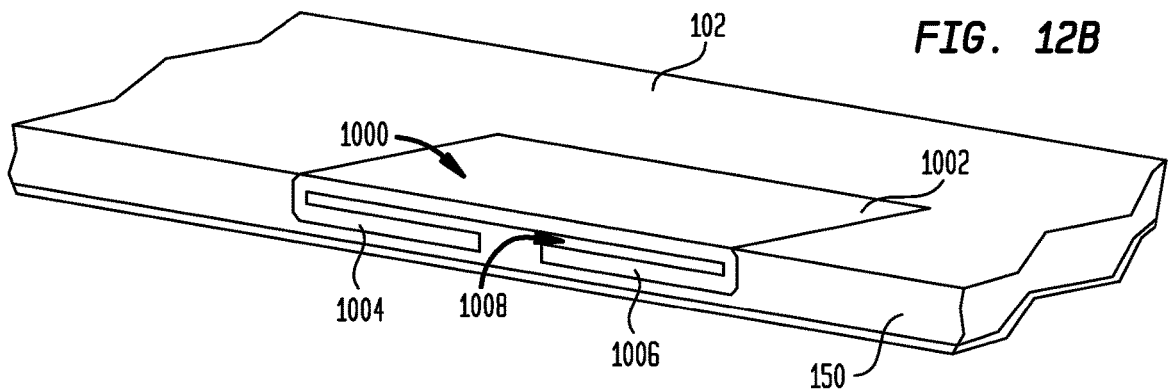
Figure 12C:
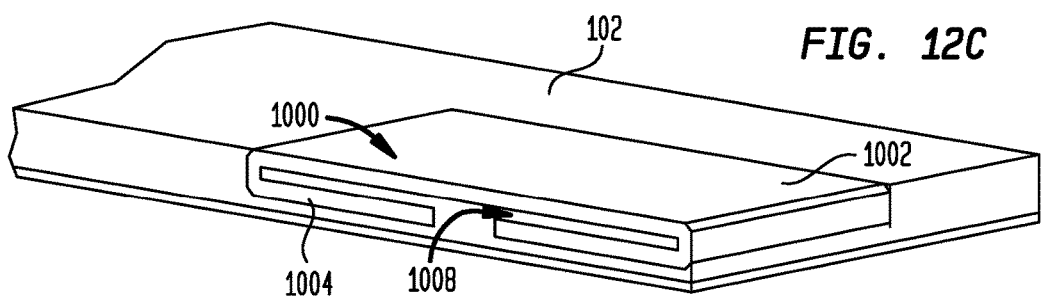

FIG. 12B shows electrode 1000 attached to sheath 102 at a position spaced from the distal tip of the sheath. Both end portions 1004 and 1006 are bent toward one another against the inner surface of plate 1002 as described above. FIG. 12C is substantially the same as FIG. 12B. However, rather than being positioned at a spaced distance from the distal tip of sheath 102, electrode 1000 in FIG. 12C is positioned at the distal tip of the sheath so that the end of the electrode is exposed on the distal end face of the sheath. As discussed above, assembling electrode 1000 to sheath 102 in this position produces the strongest signal from the bundle of His during a mapping procedure.

Figure 12D:
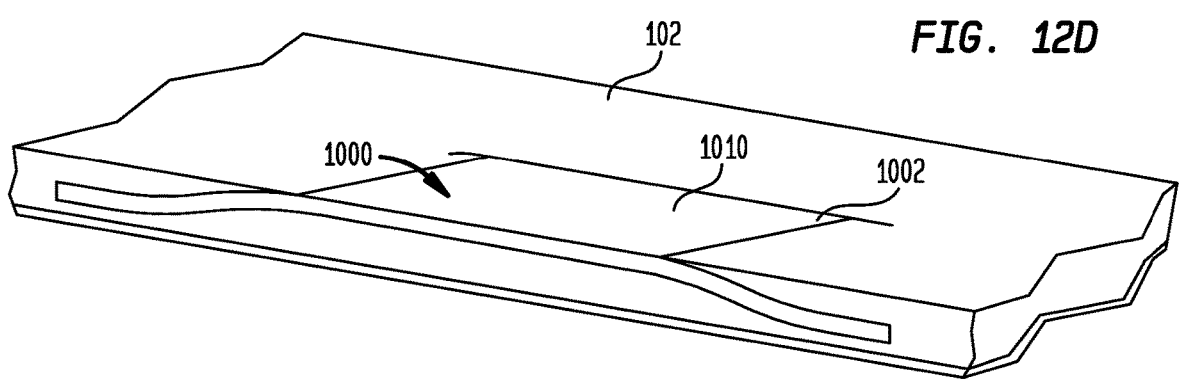

The configuration shown in FIG. 12D is similar to the configuration shown in FIG. 12A. However, rather than having one end portion bent toward the main body 1010 of plate 1002, both of end portions 1004 and 1006 are bent away from one another and away from main body 1010. Bending one or more of the end portions away from main body 1010, as shown in FIGS. 12A and 12D, facilitates the secure connection of electrode 1000 to sheath 102 as it does not require polymer to flow into the gaps 1008 between the end portions and the main portion 1010 of the electrode.

Electrode 1000 may also be affixed to sheath 102 in a variant of what has been described above in connection with FIGS. 10, 11, and 12A-12C. In each of those embodiments, at least one of end portions 1004 and 1006 is bent toward the inner surface of plate 1002, creating a gap 1008 between the end portion and the main body 1010 of the plate. In the variant contemplated, a separate strip of Pebax® or other polymer may be positioned against the inner surface of plate 1002 before the end portions are bent. Thus, after the bending operation, the strip of Pebax® or other polymer will be positioned in and fill gaps 1008. Electrode 1000 may then be assembled to sheath 102 as described above. However, during the reflow process, the sheath polymer will not have to fill gaps 1008, as those gaps will already have been filled. Rather, the polymer in gaps 1008 will melt and fuse to the other polymer of sheath 102, firmly holding electrode 1000 in place.

Figure 13:
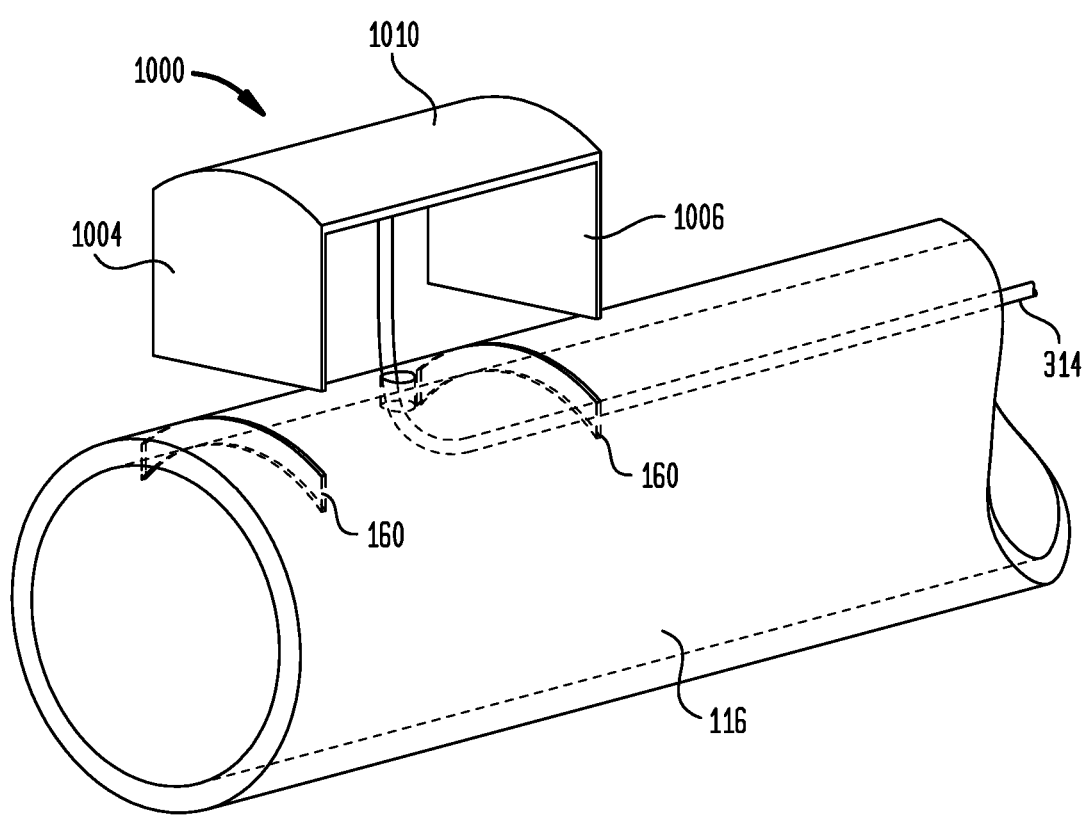
FIG. 13 is an exploded view showing a method of assembling the sheath electrode of FIG. 10 to a sheath.

Another technique for attaching electrode 1000 to sheath 102 is shown in FIG. 13. In this technique, section 116 of outer layer 114 is not assembled to sheath 102 during the sheath assembly process. Rather, slits 160 are formed at appropriate locations in section 116. The end portions 1004 and 1006 of electrode 1000 are then bent to an orientation orthogonal to the main body 1010 of the electrode. Electrode 1000 may then be assembled to sheath section 116 by inserting end portions 1004 and 1006 into slits 160 and bending them against the inner surface of the sheath section. End portions 1004 and 1006 may be bent toward one another, away from one another, or one end portion may be bent toward the main body 1010 of plate 1002, while the other end portion is bent away from the first end portion. With electrode 1000 assembled to sheath section 116 as described, the sheath section may be assembled over the distal end of sheath 102, and the distal end of the sheath may again be subjected to a reflow heating process to melt and bond sheath section 116 to the underlying braided layer 112, trapping electrode 1000 in place.

In another variant for attaching any of the electrodes described above to sheath 102, the electrode may first be sandwiched between two strips of Pebax® or other polymer. The strip of polymer on the inner surface of the electrode may include an aperture for connecting a conductor 314 to the electrode. The sandwiched electrode assembly may then be properly positioned on sheath 102 and subjected to a reflow process through which the electrode is strongly affixed to the sheath. Following the reflow process, the outer layer of polymer covering the electrode may be removed by any known technique, including laser ablation, cutting, scraping, grinding and the like to expose the outer surface of the electrode.

When delivery device 100 is being used to map the location of His bundle 30, the free ends of conductors 314 may be connected through connector 340 to a patient monitor, electrocardiograph, or other external device for displaying the electrical signals detected by electrodes 310 and 312. Optionally, sheath 102 may include a ring electrode 350 (FIG. 5B) spaced proximally of mapping electrodes 310 and 312. As ring electrode 350 comprises a continuous ring, it may be incorporated in sheath 102 during assembly of the sheath, using techniques known in the art. Electrical conductors (not shown) may extend from ring electrode 350 to connector 340 through tube 140 or through another tube incorporated in sheath 102. When available, voltage differences between ring electrode 350 and either of split ring electrodes 310 or 312 may be used to map the electrical activity of the heart.

Sheath 102 is connected at its proximal end to handle 202. A longitudinal cross-section of handle 202 is shown in FIG. 14. Handle 202 includes a distal housing portion 210 and a proximal housing portion 212, both of which are hollow. Housing portions 210 and 212 may be joined to one another by a rigid alignment rail 214 so as to maintain a space between the housing portions. Alignment rail 214 may be formed from a rigid material, such as glass-filled nylon, and may be connected to housing portions 210 and 212 by any known fastening mechanism, including screws, press fit connection, ultrasonic welding and the like. Prior to the connection of both ends of alignment rail 214 to the housing portions, a hollow pull wire screw 220 may be assembled over the rail and a rotatable actuator 222 may be assembled over the screw. Actuator 222 has a series of internal threads 224 that mate with external threads 226 on screw 220. At one end, actuator 222 has an annular ring 230 that is captured within an annular groove 232 in distal housing portion 210. At its other end, actuator 222 has a similar annular ring 234 that is captured within an annular groove 236 in proximal housing portion 212. The engagement of ring 230 in groove 232, and the engagement of ring 234 in groove 236, positions actuator 222 in the space between the housing portions, guides the rotation of the actuator in handle 202, and serves to help maintain the assembly of distal housing portion 210 to proximal housing portion 212. As actuator 222 is rotated in a first direction, pull wire screw 220 will translate proximally relative to handle 202, and when the actuator is rotated in the opposite direction, the pull wire screw will translate distally relative to the handle. The proximal end of pull wire 130 may be fed through pull wire screw 220 for connection in a known manner to the proximal end thereof. Thus, as pull wire screw 220 translates proximally, it will translate pull wire 130 proximally, and when pull wire screw 220 translates distally, it will translate pull wire 130 distally.

Handle 202 also includes a conduit 240 having a connector 242 at its proximal end for connection to a source of flushing fluid. Conduit 240 is connected to a further conduit 244 that travels through handle 202 to hub 402 for supplying the flushing fluid to flush the interior of sheath 102. Conduit 320, carrying conductors 314, is connected at one end to conduit 240 by a Y-splitter, and at the other end is connected to electrical connector 340. Conductors 314 traveling through handle 202 exit therefrom through conduits 240 and 320 and are connected by soldering or the like to pins in electrical connector 340.

Figure 15:
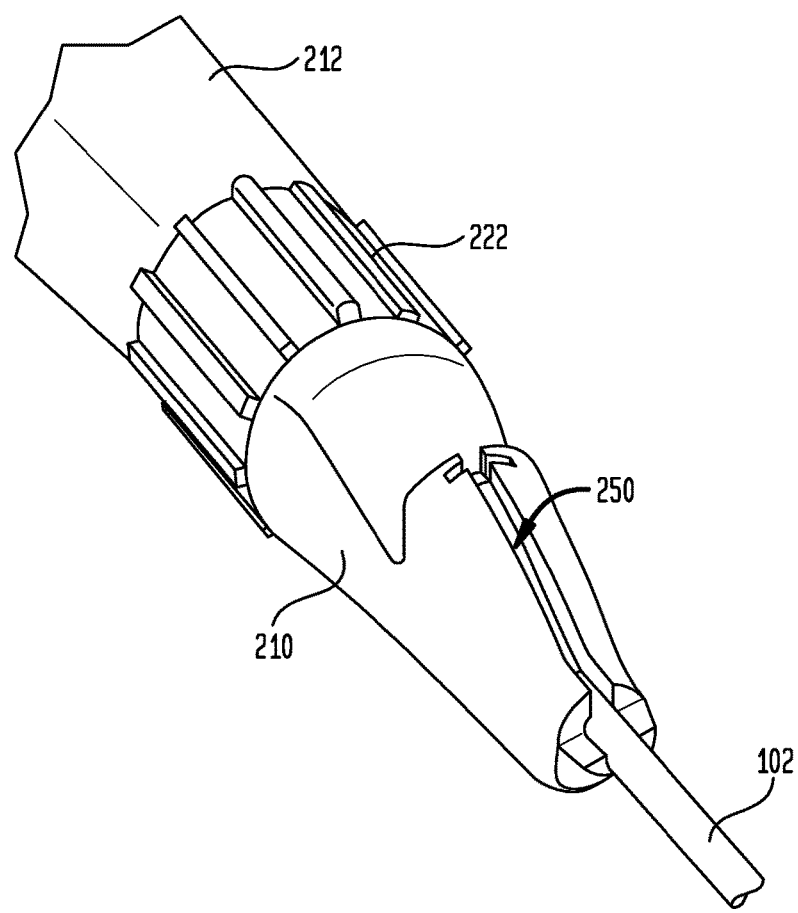
FIG. 15 is a perspective view of the distal end of the delivery device handle showing the slitting channel.

Referring to FIG. 14, hub 402 is held in the interior of distal housing portion 210 and fixedly connects the proximal end of sheath 102 to handle 202. Sheath 102 passes through a hemostasis valve 404 in hub 402, which provides a seal to minimize blood loss from around the sheath. A channel 250 (FIG. 15) formed in the upper surface of distal housing portion 210 provides access to hub 402 and sheath 102. Channel 250 is adapted to receive a sheath slitter for slitting sheath 102 following the insertion of the pacing lead in a patient, as will be explained more fully below.

Figure 16:
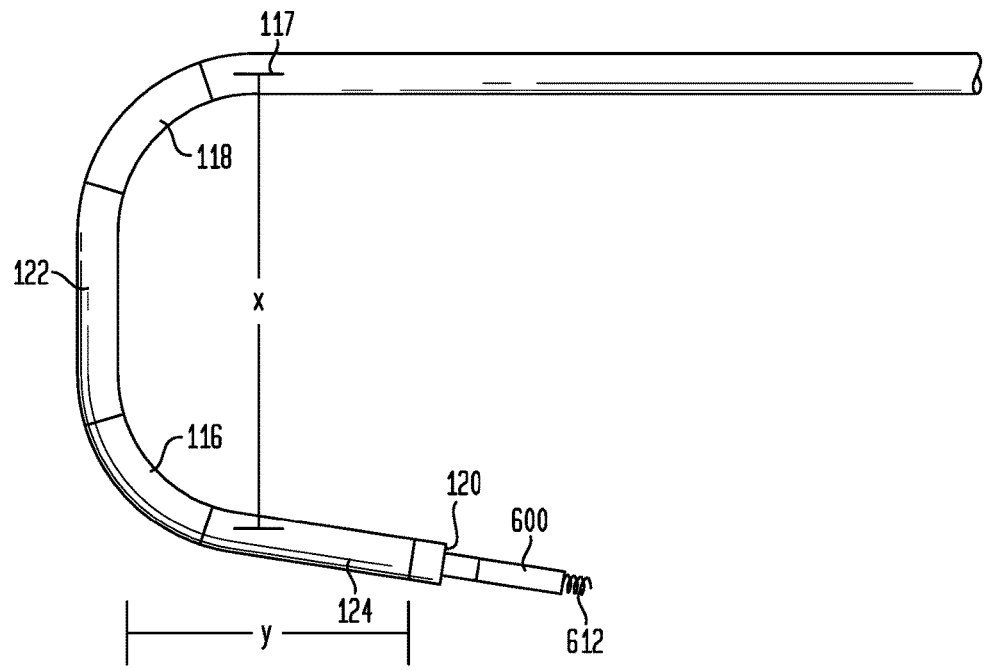
FIG. 16 is an enlarged view of the distal end of the delivery device sheath in a deflected condition.
Figure 20:
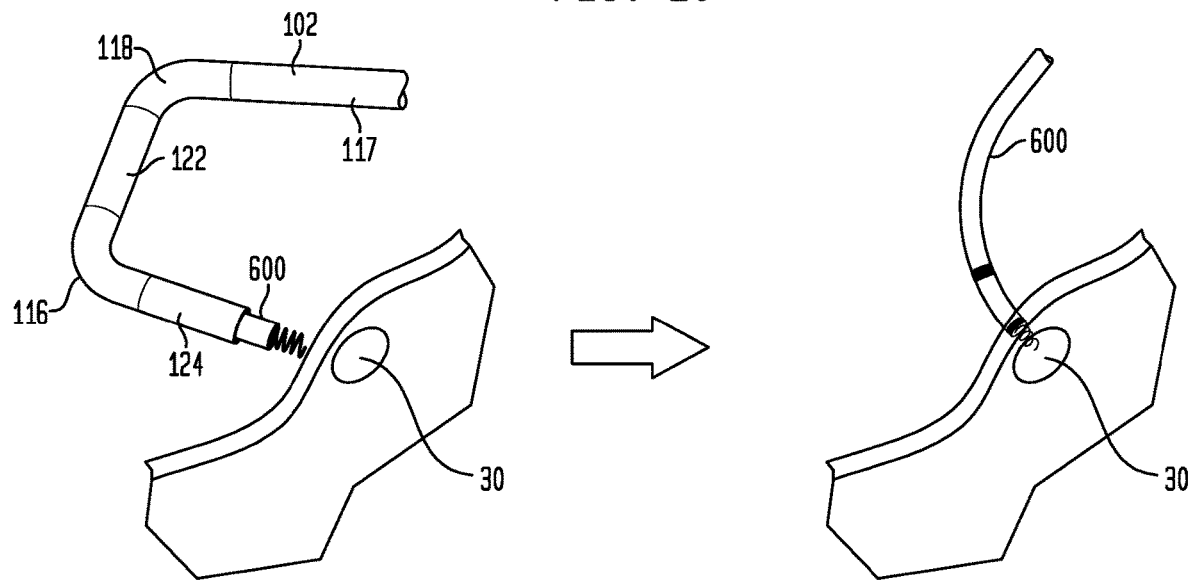
FIG. 20 is a diagrammatic view showing the use of the delivery device of FIG. 4 to locate and implant a pacing lead in the bundle of His.
Figure 17:
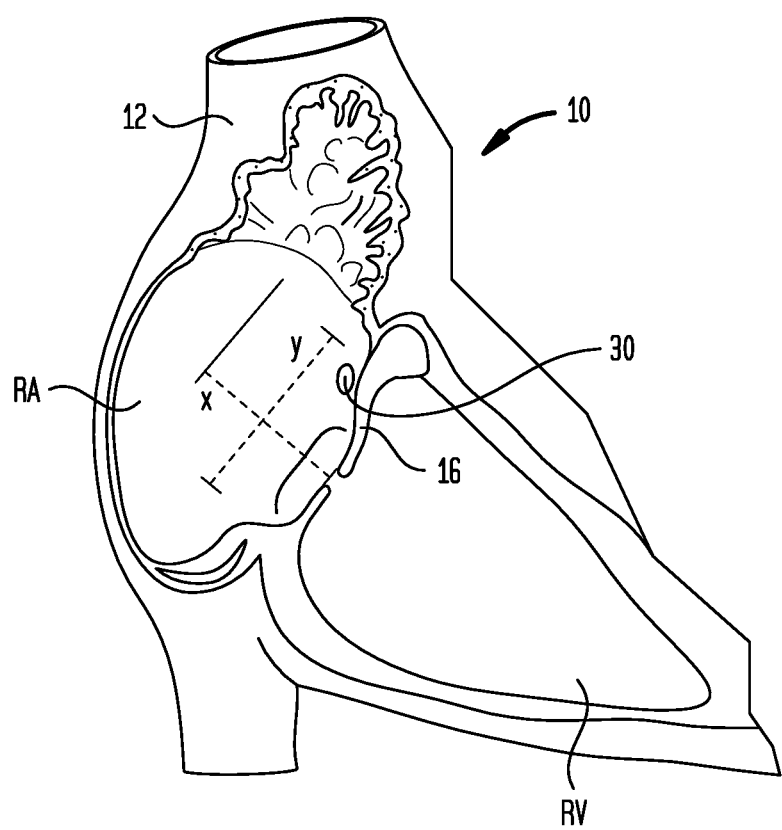
FIG. 17 is a diagrammatic view showing certain distances relative to structures in the heart.

When pull wire 130 is translated proximally, the pliability of sections 116 and 118 enables the distal portion of sheath 102 to deflect from a substantially straight configuration to the predefined dual hinged configuration shown in FIG. 16. By deflecting at these two spaced locations, sheath 102 assumes a shape that better enables its distal end 120 to be positioned to confront the right atrial wall near His bundle 30 while the proximal section 115 of the sheath is positioned within the superior vena cava 12 of heart 10. Distance X in FIG. 16 is the average distance from the central axis of superior vena cava 12, through which sheath 102 enters the right atrium RA, to tricuspid valve 16, while distance Y is the average inner diameter of the tricuspid valve. One-third of distance Y approximates the distance which sheath 102 must traverse to reach the atrial wall in order to contact or come in close proximity to His bundle 30. As this distance is an approximation, and as exceeding this distance is not likely to have a negative effect on locating His bundle 30, it will be appreciated that this distance (which is approximately the distance from the section 122 of sheath 102 to the distal end 120 thereof) may be between about ⅓ Y and about ½ Y. Distances X and Y are illustrated relative to the structures of heart 10 in the diagrammatic illustration shown in FIG. 17. To complete the description, rotating actuator 222 in the opposite direction will translate pull wire 130 distally, returning sheath 102 toward the substantially straight configuration.

Figure 18:
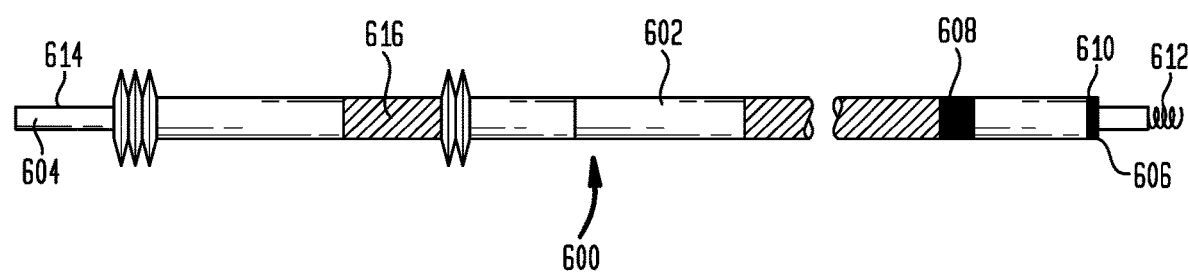
FIG. 18 is a highly schematic side view of a pacing lead.

Delivery device 100 may be used to deliver a pacing lead into the right atrium RA, to map the right atrium to locate His bundle 30, and to fix the pacing lead therein. One example of such a pacing lead is pacing lead 600 shown schematically in FIG. 18. Lead 600 generally has a flexible elongate body 602 with a proximal end 604, a distal end 606, and a lumen (not shown) extending axially therethrough. A pair of bipolar electrodes 608, 610 is located at the distal end of body 602. Electrode 610 is positioned at the distal tip of body 602, while electrode 608 may be spaced therefrom along the length of the body. A fixation anchor 612 extends distally from the distal end 606 of body 602 and forms a part of electrode 610. At the proximal end 604 of body 602, lead 600 includes a pair of electrical contacts 614 and 616. Contacts 614 and 616 are each electrically connected to one of electrodes 608 and 610 by conductors traveling through the lumen in body 602. Contacts 614 and 616 enable pacing lead 600 to be mechanically and electrically connected to pacemaker 52, such as by alligator clips or other connectors connected to contacts 614 and 616.

The use of delivery device 100 to deliver and fix pacing lead 600 in the bundle of His will now be described with reference to FIGS. 19A-D and 20. FIGS. 19A-D illustrate the delivery and fixation of pacing lead 600 with respect to an anatomically-accurate transparent model 700 of the right side of the human heart. Model 700 may be used to train operators in the His pacing procedure, and to develop and test clinical tools for performing the procedure. For clarity, the reference numerals used in FIGS. 19A-D to identify the structures of the heart will be the same reference numbers used to identify the structures in the cutaway view of the heart illustrated in FIG. 1. The region in which the bundle of His is located is simulated in model 700 by a conductive insert (not shown) that may be received in port 710. The insert may be formed of a gel to enable fixation of pacing lead 600 therein, and may have physical and/or electrical properties that simulate myocardial tissue. The insert may also be doped with an ionic material to provide electrical properties similar to those of the His bundle so that electrically-active delivery devices can be used to map the region. During a mapping and fixation procedure, the insert may be stimulated electrically by a circuit to produce an electric signal, preferably one that is similar to that produced by the bundle of His. A more detailed description of model 700 and its use can be found in commonly owned U.S. patent application Ser. No. 16/208,348, the disclosure of which is hereby incorporated by reference herein.

Figure 19A:
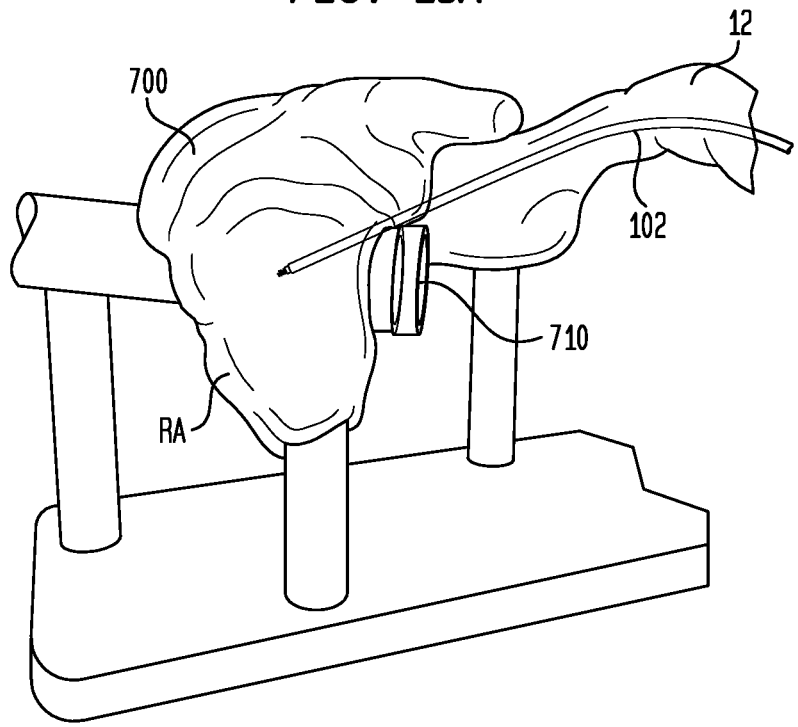
FIGS. 19A-D illustrate a process by which the delivery device of FIG. 4 locates the bundle of His and implants a pacing lead therein.
Figure 19B:
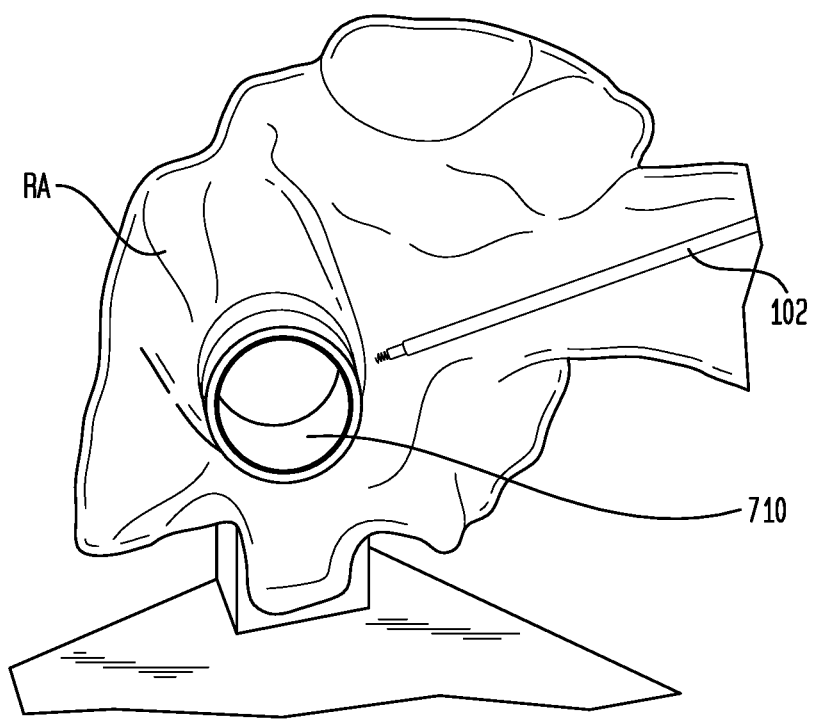

With electrical conductors 314 electrically connected through connector 340 to an external device for receiving signals from electrodes 310 and 312, delivery device 100 is inserted through a vascular access site into the superior vena cava 12, and is maneuvered through the superior vena cava to the right atrium RA as illustrated in FIGS. 19A and 19B. During this insertion procedure, the sheath 102 of delivery device 100 may have a substantially straight configuration, and may include a dilator (not shown) positioned in lumen 126 thereof to enlarge the access path and to provide support to the sheath as it is being maneuvered. The straight configuration of sheath 102 facilitates its passage through the superior vena cava 12 and into the right atrium RA. Once the distal end 120 of delivery device 100 has entered the right atrium RA, the dilator may be removed from the delivery device and pacing lead 600 may be inserted into lumen 126 in its place. Again, the straight configuration of sheath 102 facilitates the insertion of pacing lead 600 therein.

Figure 19C:
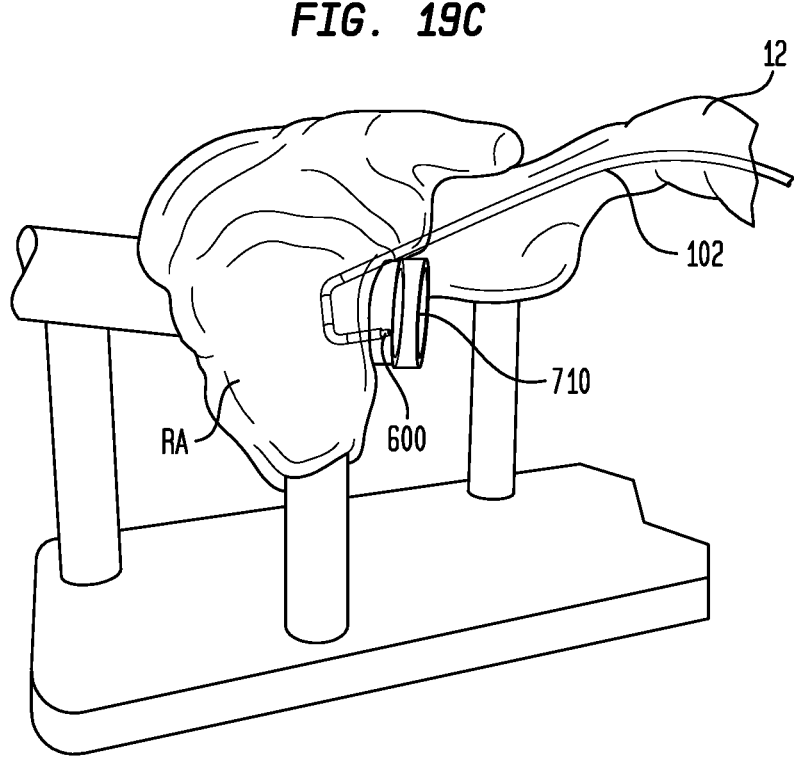
Figure 19D:
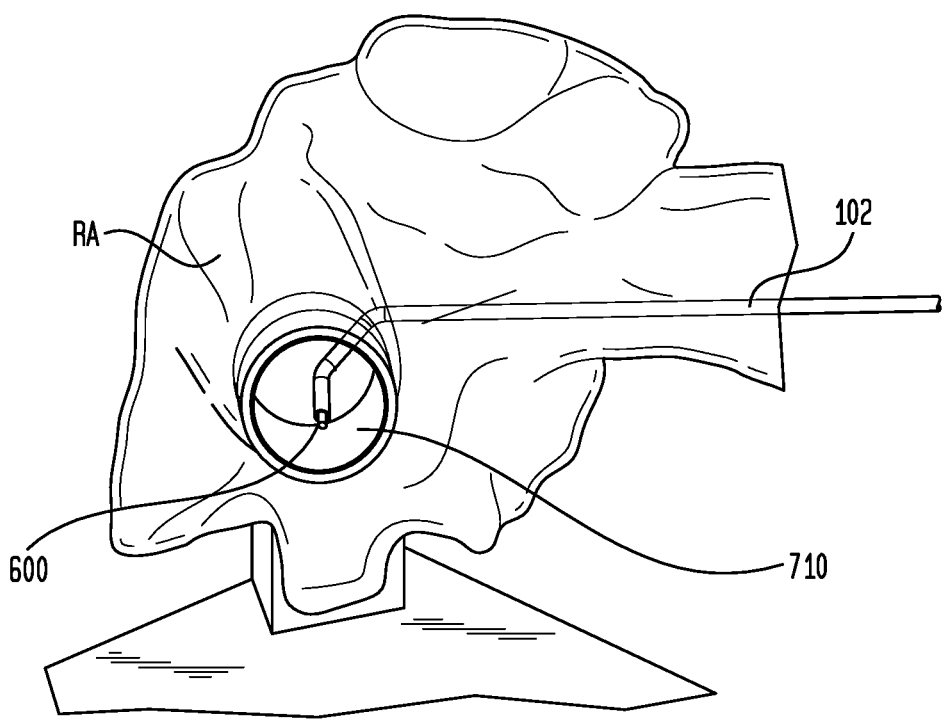

With the distal portion of sheath 102 fully within right atrium RA, the user may operate delivery device 100 to place sheath 102 in the deflected configuration shown in FIG. 19C. Since sheath 102 is only able to deflect in a single direction, the user must first confirm that delivery device 100 is in the proper orientation. This may be accomplished by locating the position of indicia (not shown) at the proximal end of sheath 102 or on handle 202, by the nonsymmetrical shape of the handle or by another indicator. Such indicator preferably will identify the side of sheath 102 on which pull wire 130 is located, which is the direction to which the distal portion of the sheath will deflect. Once the proper orientation of sheath 102 has been confirmed, the user may operate the actuator 222 on the handle 202 of delivery device 100 to move the distal portion of the sheath to the deflected configuration. With the proximal section 115 of sheath 102 positioned in the superior vena cava 12 and the distal portion of the sheath deflected as shown in FIG. 19C, the distal end 120 of the sheath will point generally toward the region in the atrial septum at which the bundle of His 30 is located, and will be in close proximity to the septum, as shown in FIG. 19D. If electrical signals are received from electrodes 310 and 312 in this position of sheath 102, the user will know that the distal end 120 of the sheath is aligned with His bundle 30.

If electrodes 310 and 312 are not receiving electrical signals, or if the signals are very faint, the user can maneuver the distal end 120 of sheath 102 by small movements of actuator 222 in either a forward or reverse direction to scan the atrial wall. These small movements of actuator 222 will deflect the distal portion of sheath 102 by small amounts toward or away from the proximal section 115 of the sheath.

Scanning in different directions can be accomplished by small rotations of handle 202. When the signals received by electrodes 310 and 312 are the strongest, the user can be confident that His bundle 30 has been located, and the close proximity of the electrodes to one another will assure that the His bundle is directly opposite the distal end 120 of sheath 102. With each of these movements, the distal end 120 of sheath 102 remains generally perpendicular to the atrial wall. Accordingly, once this mapping procedure has located the bundle of His, pacing lead 600 can be fixed in the His bundle by advancing the fixation anchor 612 of the lead out from the distal end 120 of sheath 102 and rotating the lead within delivery device 100 to drive the fixation anchor into the atrial septal wall, as shown schematically in FIG. 20. Since the overall stiffness of sheath 102 is relatively high, the distal tip of the sheath will maintain its position as fixation anchor 612 is driven into the atrial septal wall, thereby assuring that the fixation anchor will not be diverted from its target site.

Figure 21:
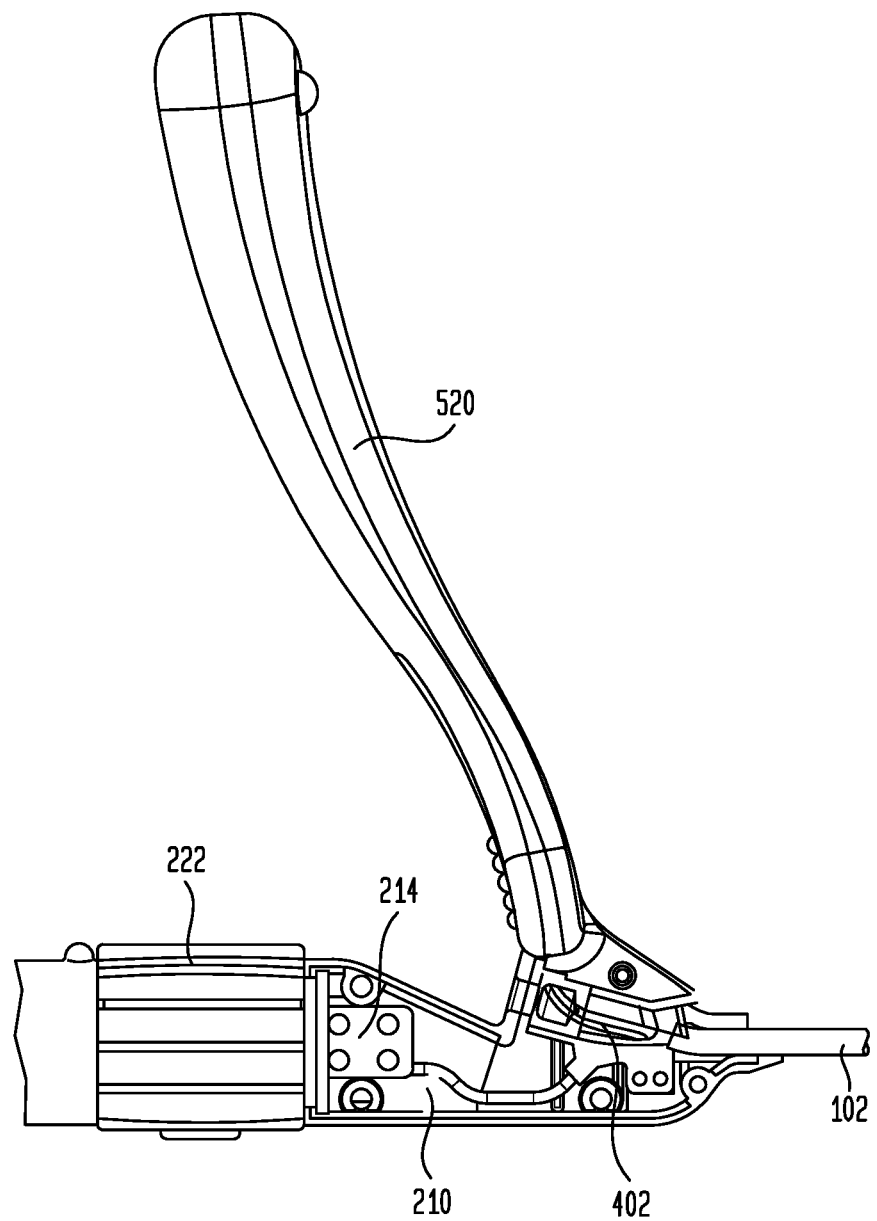
FIG. 21 is a partial view showing a sheath slitter attached to the distal housing portion of the delivery device handle.

Once lead 600 has been properly fixed in the tissue of the bundle of His, sheath 102 can be returned to a substantially straight configuration by rotating actuator 222 in the direction opposite that used for deflection. Sheath 102 may then be removed from around lead 600 and from heart 10. This may be accomplished by assembling a sheath slitter 520 to the distal housing portion 210 of housing 202 so that the knife blade thereof is positioned within channel 250, as shown in FIG. 21. By holding sheath slitter 520 in a substantially stationary position while pulling delivery device 100 proximally, the knife blade of the sheath slitter will slice through hub 402 and along sheath 102, without damaging lead 600. When it reaches electrodes 310 and 312, the knife blade of slitter 520 will pass between the electrodes to the distal end 120 of sheath 102. Once sheath 102 has been split along its entire length, the sheath may be removed, leaving lead 600 embedded within the atrial septal wall at the bundle of His 30.

Figure 22A:
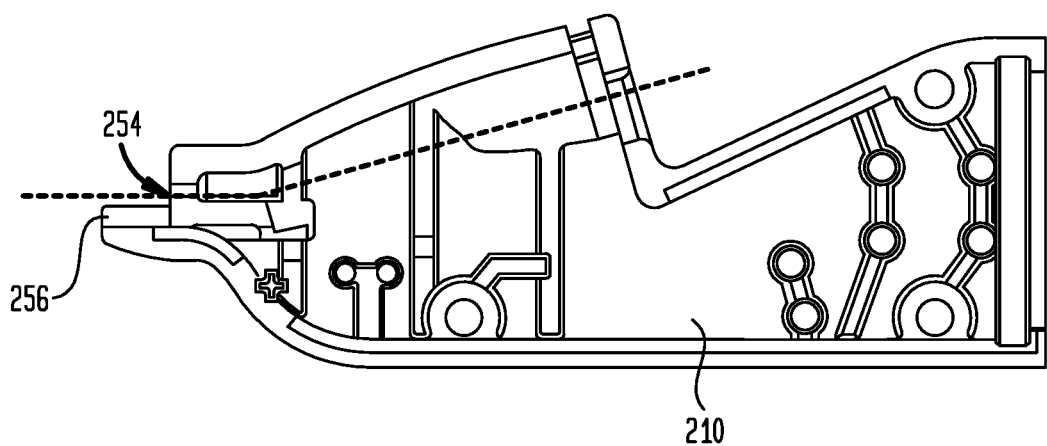
FIG. 22A is a longitudinal cross-section through the distal housing portion of the delivery device handle shown in FIG. 14.
Figure 22B:
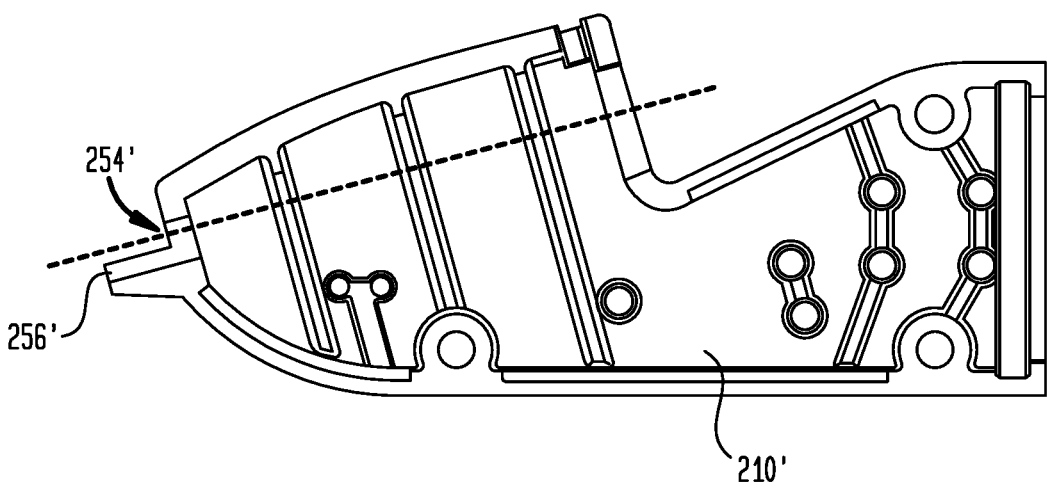
FIG. 22B is a longitudinal cross-section through the distal housing portion of a delivery device handle according to another embodiment of the disclosure.

In a variant hereof, delivery device 100 may include a distal housing portion 210', which is an alternate embodiment of distal housing portion 210. A cross-sectional view of distal housing portion 210 is shown in FIG. 22A and a cross-sectional view of distal housing portion 210' is shown in FIG. 22B. Distal housing portion 210' is substantially similar to distal housing portion 210, with the exception of the angle at which sheath 102 enters handle 202. In distal housing portion 210, sheath 102 enters the distal housing portion through an aperture 254 and along a guide surface 256 that are oriented substantially parallel to the longitudinal axis of handle 202. In contrast, sheath 102 enters distal housing portion 210' through an aperture 254' and along a guide surface 256' that are substantially parallel to the central longitudinal axis of hub 402. In both embodiments, sheath 102 exits housing portion 210, 210' along an axis that is parallel to the longitudinal axis of hub 402. As a result, while distal housing portion 210 creates a bend in sheath 102 for sheath slitter 520 to encounter in the initial stages of the slitting operation, distal housing portion 210' presents the slitter with a substantially straight sheath.

To summarize the foregoing, according to a first aspect of the disclosure, a delivery device for delivering a pacing lead to the His bundle of a patient's heart includes a handle; an elongated sheath having a proximal end connected to the handle and a distal end remote from the handle, a distal portion of the sheath having a plurality of flexible sections spaced from one another along a length of the sheath; a pull wire having a distal end connected to the sheath distally of the flexible sections and extending to a proximal end; and a plurality of mapping electrodes positioned at the distal end of the sheath; and or the distal end of the sheath may have a distal tip, and the mapping electrodes may include two electrodes that diametrically oppose one another at a position spaced from the distal tip of the sheath; and/or the two electrodes may be spaced apart by between about 1 mm and about 3 mm in a circumferential direction of the sheath; and/or the distal end of the sheath may have a distal end face, and the mapping electrodes may be exposed on the distal end face; and/or the distal end of the sheath may have a distal end face, and the mapping electrodes may be spaced from the distal end face; and/or the flexible portions of the sheath may have a first Shore D hardness which is less than a second Shore D hardness of remaining portions of the sheath; and/or the flexible portions of the sheath may have a Shore D hardness of between about 20 and about 40; and/or the flexible portions of the sheath may have a Shore D hardness of about 35; and/or the remaining portions of the sheath may have a Shore D hardness of between 60 and about 100; and/or the remaining portions of the sheath may have a Shore D hardness of between 70 and about 75; and/or the sheath may have a substantially straight configuration in an initial condition and a dual hinged curved configuration in a use condition; and/or the handle may include a rotatable actuator, rotation of the actuator in a first direction moving the sheath toward the use condition and rotation of the actuator in an opposite direction moving the sheath toward the initial condition; and/or the handle may include a rotatable portion and translatable portion, the proximal end of the pull wire being connected to the translatable portion, whereby rotation of the rotatable portion translates the pull wire in a longitudinal direction of the sheath; and/or the handle may include a proximal handle portion and a distal handle portion, the proximal handle portion being connected to the distal handle portion by a rail so as to define a space between the proximal handle portion and the distal handle portion; and/or the rotatable actuator may be connected to the handle between the proximal handle portion and the distal handle portion; and/or the handle may have a longitudinal axis and the proximal end of the sheath may enter the handle along the longitudinal axis and may exit the handle at an angle transverse to the longitudinal axis; and/or the handle may have a longitudinal axis and the proximal end of the sheath may enter the handle at a predetermined angle transverse to the longitudinal axis and may exit the handle at the predetermined angle transverse to the longitudinal axis; and/or each of the mapping electrodes may include a pair of side edges substantially parallel to a longitudinal axis of the sheath and a pair of end edges substantially orthogonal to the longitudinal axis of the sheath, and the side edges may be beveled; and/or each of the electrodes may be formed from a plate having a pair of opposed side edges and a pair of opposed end edges, and the plate may have a thickness along the side edges and along the end edges that is less than the thickness in a center of the plate; and/or each of the electrodes may have a main body and a pair of end portions projecting from opposite ends of the main body; and/or the end portions may project away from the main body in opposite directions; and/or the main body may have an inner surface and an outer surface, and at least one of the end portions may be bent against the inner surface of the main body; and/or the pair of end portions may be bent toward one another and toward the inner surface of the main body; and/or the sheath may include a first layer, a middle layer, and an outer layer; and/or the inner layer may extend from the proximal end of the sheath to the distal end of the sheath; and/or the inner layer may be formed from a lubricious material; and/or the lubricious material may be polytetrafluoroethylene; and/or the middle layer may be a braided layer including metallic braids embedded within a polymer; and/or the braided layer may extend from the proximal end of the sheath to the distal end of the sheath; and/or the outer layer may include a plurality of sections formed from a polymer having a first shore D hardness and a plurality of sections formed from a polymer having a second shore D hardness which is greater than the first shore D hardness; and/or the use condition of the sheath may define a deflection plane, and the mapping electrodes may include two electrodes that are positioned on the sheath so that the two electrodes lie within the deflection plane in the use condition.

According to another aspect of the disclosure, a method for delivering a pacing lead to the His bundle of a patient's heart includes providing a delivery device having a sheath with an axial lumen and a distal end face; inserting the sheath into the patient's body through the superior vena cava until a distal end portion of the sheath is positioned in the right atrium of the patient; inserting a pacing lead into the axial lumen of the sheath; deflecting the distal end portion of the sheath so that the distal end face of the sheath confronts the wall of the right atrium; and moving the distal end face of the sheath relative to the wall of the right atrium until electrodes adjacent the distal end face of the sheath receive electrical signals from the bundle of His; and/or the delivery device may include a handle connected to a proximal end of the sheath and a pull wire extending from the handle to a distal end of the sheath, and the deflecting step may include translating the pull wire proximally relative to the handle; and/or the handle may include a rotatable actuator, and the deflecting step may include rotating the actuator in a first direction to move the pull wire proximally relative to the handle; and/or the distal end portion of the sheath may include a plurality of flexible sections spaced from one another along a length of the sheath, and the deflecting step may include bending the sheath at the flexible sections to place the distal end portion of the sheath in a dual hinged curved configuration; and/or the method may further include the step of fixing the pacing lead to tissue in the bundle of His.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims. For example, although the delivery device has been described herein for use in mapping the bundle of His and fixing a pacing lead therein, the delivery device may also be used as a component of an ablation catheter to ablate the bundle of His. In such event, the heart could be paced using multiple leads in various chambers of the heart.

The invention claimed is:

1. A delivery device for delivering a pacing lead to the His bundle of a patient's heart, the delivery device comprising:
   a handle;
   an elongated sheath having a proximal end connected to the handle and a distal end remote from the handle, a distal portion of the sheath having in series from the distal end a first relatively rigid section, a first relatively flexible section, a second relatively rigid section, a second relatively flexible section and a third relatively rigid section, the first relatively flexible section being spaced apart from the second relatively flexible section such that the distal portion is deflectable to a dual hinged configuration, the first, second, and third relatively rigid sections being formed from a first polymer having a first Shore D hardness, and the first and second relatively flexible sections being formed from a second polymer having a second Shore D hardness less than the first Shore D hardness;
   a pull wire having a distal end connected to the sheath distally of the first relatively flexible section and extending to a proximal end of the pull wire;
   a plurality of mapping electrodes positioned at the distal end of the sheath;
   an electrical conductor extending from each of the plurality of mapping electrodes; and
   a tube extending along a length of the elongated sheath, wherein the electrical conductors extend through the tube.

2. The delivery device as claimed in claim 1, wherein the distal end of the sheath has a distal tip, and the mapping electrodes include two electrodes that diametrically oppose one another at a position spaced from the distal tip of the sheath.

3. The delivery device as claimed in claim 2, wherein the two electrodes are spaced apart by between 1 mm and 3 mm in a circumferential direction of the sheath.

4. The delivery device as claimed in claim 1, wherein the distal end of the sheath has a distal end face, and the mapping electrodes are exposed on the distal end face.

5. The delivery device as claimed in claim 1, wherein the distal end of the sheath has a distal end face, and the mapping electrodes are spaced from the distal end face.

6. The delivery device as claimed in claim 1, wherein the second Shore D hardness is between 20 and about 40.

7. The delivery device as claimed in claim 1, wherein the second Shore D hardness is 35.

8. The delivery device as claimed in claim 1, wherein the first Shore D hardness is between 60 and about 100.

9. The delivery device as claimed in claim 1, wherein the first Shore D hardness is between 70 and 75.

10. The delivery device as claimed in claim 1, wherein the sheath has a substantially straight configuration in an initial condition and the dual hinged configuration in a use condition.

11. The delivery device as claimed in claim 1, wherein the handle includes a proximal handle portion and a distal handle portion, the proximal handle portion being connected to the distal handle portion by a rail so as to define a space between the proximal handle portion and the distal handle portion.

12. The delivery device as claimed in claim 11, further comprising a rotatable actuator positioned in the space and connected to the proximal handle portion and the distal handle portion, rotation of the actuator in a first direction moving the sheath toward a use condition and rotation of the actuator in an opposite direction moving the sheath toward an initial condition.

13. A delivery device for delivering a pacing lead to the His bundle of a patient's heart, the delivery device comprising:
- a handle;
- an elongated sheath having a proximal end connected to the handle and a distal end remote from the handle, a distal portion of the sheath having a plurality of flexible sections spaced from one another along a length of the sheath;
- a pull wire having a distal end connected to the sheath distally of the flexible sections and extending to a proximal end of the pull wire; and
- a plurality of mapping electrodes positioned at the distal end of the sheath,
- wherein the handle has a longitudinal axis and the proximal end of the sheath enters the handle at a first position at a predetermined angle transverse to the longitudinal axis and exits the handle at a second position at the predetermined angle transverse to the longitudinal axis.

14. A delivery device for delivering a pacing lead to the His bundle of a patient's heart, the delivery device comprising:
- a handle;
- an elongated sheath having a proximal end connected to the handle and a distal end remote from the handle, the distal end having a distal tip, a distal portion of the sheath having a plurality of flexible sections spaced from one another along a length of the sheath;
- a pull wire having a distal end connected to the sheath distally of the flexible sections and extending to a proximal end of the pull wire;
- a plurality of mapping electrodes positioned at the distal end of the sheath, the mapping electrodes including two electrodes that diametrically oppose one another at a position spaced from the distal tip of the sheath,
- an electrical conductor extending from each of the plurality of mapping electrodes; and
- a tube extending along a length of the elongated sheath, wherein the electrical conductors extend through the tube,
- wherein the distal portion of the sheath is deflectable within a deflection plane, and the two electrodes lie within the deflection plane when the distal portion of the sheath is deflected.

\* \* \* \* \*